US012576038B2

(12) United States Patent
Ishihara et al.

(10) Patent No.: US 12,576,038 B2
(45) Date of Patent: Mar. 17, 2026

(54) COMPOSITION, LIPID PARTICLE MANUFACTURING KIT, SUBSTANCE DELIVERY METHOD, AND DETECTION METHOD

(71) Applicants: SHINSHU UNIVERSITY, Matsumoto (JP); KABUSHIKI KAISHA TOSHIBA, Tokyo (JP)

(72) Inventors: Mitsuko Ishihara, Setagaya (JP); Eiichi Akahoshi, Shinagawa (JP); Yozo Nakazawa, Matsumoto (JP); Shoji Saito, Matsumoto (JP)

(73) Assignees: SHINSHU UNIVERSITY, Matsumoto City (JP); KABUSHIKI KAISHA TOSHIBA, Tokyo (JP)

( * ) Notice: Subject to any disclaimer, the term of this patent is extended or adjusted under 35 U.S.C. 154(b) by 954 days.

(21) Appl. No.: 17/472,173

(22) Filed: Sep. 10, 2021

(65) Prior Publication Data

US 2022/0047517 A1 Feb. 17, 2022

Related U.S. Application Data

(63) Continuation of application No. PCT/IB2020/058307, filed on Sep. 7, 2020.

(30) Foreign Application Priority Data

Mar. 19, 2020 (JP) ................................ 2020-049219

(51) Int. Cl.
*A61K 9/50* (2006.01)
*A61K 31/7105* (2006.01)
*G01N 33/574* (2006.01)

(52) U.S. Cl.
CPC ........ *A61K 9/5015* (2013.01); *A61K 31/7105* (2013.01); *G01N 33/574* (2013.01)

(58) Field of Classification Search
None
See application file for complete search history.

(56) References Cited

U.S. PATENT DOCUMENTS

| | | | | |
|---|---|---|---|---|
| 11,548,857 | B2 * | 1/2023 | Ishihara | C07D 251/04 |
| 2011/0250225 | A1 * | 10/2011 | Fotin-Mleczek | A61P 31/00 424/193.1 |
| 2013/0259923 | A1 | 10/2013 | Bancel et al. | |
| 2014/0206753 | A1 * | 7/2014 | Guild | A61K 9/5123 514/44 R |
| 2015/0157565 | A1 | 6/2015 | Heartlein et al. | |
| 2020/0270217 | A1 | 8/2020 | Ishihara et al. | |

FOREIGN PATENT DOCUMENTS

| | | | |
|---|---|---|---|
| JP | 2015-520195 | A | 7/2015 |
| WO | WO 2006/099667 | A1 | 9/2006 |
| WO | WO 2010/037408 | A1 | 4/2010 |
| WO | WO 2020/039631 | A1 | 2/2020 |

OTHER PUBLICATIONS

Ahern, Holly. Biochemical, Reagent Kits Offer Scientists Good Return on Investment. The scientist, vol. 9, p. 20, Jul. 24, 1995. (retrieved from https://www.the-scientist.com/technology/biochemical-reagents-kits-offer-scientists-good-return-on-investment-58425) (Year: 1995).*

Keiya Ozawa, "Gene therapy for hematopoietic malignancies", Journal of Clinical and Experimental Medicine (vol. 202, No. 1), 2002, pp. 108-112 (with English Translation).

Written Opinion issued Nov. 16, 2020 in PCT/IB2020/058307 filed on Sep. 7, 2020, 6 pages.

Lamichhane et al., "Liposomes: Clinical Applications and Potential for Image-Guided Drug Delivery", Molecules, vol. 23, No. 2, 2018, 17 pages, DOI: 10.3390/molecules23020288.

Fleischer et al., "Targeting T cell malignancies using CARbased immunotherapy: challenges and potential solutions", Journal of Hematology & Oncology, vol. 12, No. 1, 2019, 21 pages, DOI: 10.1186/s13045-019-0801-y.

Mamonkin, Maksim et al., "A T-cell-directed chimeric antigen receptor for the selective treatment of T-cell malignancies", Blood vol. 126, No. 8, 2015, pp. 983-992, DOI: 10.1182/blood-2015-02-629527.

Rossignoli et al., "Inducible Caspase9-mediated suicide gene for MSC-based cancer gene therapy", Cancer Gene Therapy, vol. 26, No. 1, 2019, pp. 11-16, DOI: 10.1038/s41417-018-0034-1.

Song et al., "Cancer gene therapy with iCaspase-9 transcriptionally targeted to tumor endothelial cells", Cancer Gene Therapy (Author Manuscript), pp. 1-15, Published in final edited form as: Cancer Gene Therapy, vol. 15, No. 10, 2008, pp. 667-675, DOI: 10.1038/cgt.2008.38.

Communication Under Rule 71(3) EPC, issued on Apr. 14, 2025 in corresponding European Application No. 20775943.2.

Nakazawa, Y., et al.; "Optimization of the PiggyBac Transposon System for the Sustained Genetic Modification of Human T-Lymphocytes"; J Immunother.Oct. 2009; 32(8): 826-836. doi:10.1097/CJI.0b013e3181ad762b.; NIH Public Access Author Manuscript, (18 pages).

Straathof, Karin C., et al., "An inducible caspase 9 safety switch for T-cell therapy"; Blood, Jun. 1, 2005; pp. 4247-4254, vol. 105, No. 11, DOI: 10.1182/blood-2004-11-4564. (8 pages).

* cited by examiner

*Primary Examiner* — Ali Soroush
*Assistant Examiner* — Afua Bamfoaa Boateng
(74) *Attorney, Agent, or Firm* — Oblon, McClelland, Maier & Neustadt, L.L.P.

(57) ABSTRACT

According to one embodiment, a composition is for delivering an objective substance to the T-cell malignant tumor cell. The composition contains a substance delivery carrier. The substance delivery carrier has a lipid particle, and the objective substance encapsulated in the lipid particle. The lipid particle contains, as constituents thereof, at least a first lipid represented by formula (I) and a second lipid represented by formula (II).

22 Claims, 9 Drawing Sheets

Specification includes a Sequence Listing.

SEQUENCE LISTING

```
<160> NUMBER OF SEQ ID NOS: 8

<210> SEQ ID NO 1
<211> LENGTH: 20
<212> TYPE: PRT
<213> ORGANISM: artificial
<220> FEATURE:
<223> OTHER INFORMATION: Nucleic acid condensing peptide

<400> SEQUENCE: 1

Arg Gln Arg Gln Arg Tyr Tyr Arg Gln Arg Gln Arg Gly Gly Arg Arg
1               5                   10                  15

Arg Arg Arg Arg
            20


<210> SEQ ID NO 2
<211> LENGTH: 13
<212> TYPE: PRT
<213> ORGANISM: artificial
<220> FEATURE:
```

-continued

<223> OTHER INFORMATION: Nucleic acid condensing peptide

<400> SEQUENCE: 2

Arg Gln Arg Gln Arg Gly Gly Arg Arg Arg Arg Arg Arg
1 5 10

<210> SEQ ID NO 3
<211> LENGTH: 21
<212> TYPE: PRT
<213> ORGANISM: artificial
<220> FEATURE:
<223> OTHER INFORMATION: nucleic acid condensing peptide

<400> SEQUENCE: 3

Arg Arg Arg Arg Arg Arg Tyr Tyr Arg Gln Arg Gln Arg Gly Gly Arg
1 5 10 15

Arg Arg Arg Arg Arg
20

<210> SEQ ID NO 4
<211> LENGTH: 39
<212> TYPE: PRT
<213> ORGANISM: artificial
<220> FEATURE:
<223> OTHER INFORMATION: Nucleic acid condensing peptide

<400> SEQUENCE: 4

Gly Asn Gln Ser Ser Asn Phe Gly Pro Met Lys Gly Gly Asn Phe Gly
1 5 10 15

Gly Arg Ser Ser Gly Pro Tyr Gly Gly Gly Gly Gln Tyr Phe Ala Lys
20 25 30

Pro Arg Asn Gln Gly Gly Tyr
35

<210> SEQ ID NO 5
<211> LENGTH: 516
<212> TYPE: DNA
<213> ORGANISM: Oplophorus gracilirostrius

<400> SEQUENCE: 5
atggtcttca cactcgaaga tttcgttggg gactggcgac agacagccgg ctacaacctg 60
gaccaagtcc ttgaacaggg aggtgtgtcc agtttgtttc agaatctcgg ggtgtccgta 120
actccgatcc aaaggattgt cctgagcggt gaaaatgggc tgaagatcga catccatgtc 180
atcatcccgt atgaaggtct gagcggcgac caaatgggcc agatcgaaaa aatttttaag 240
gtggtgtacc ctgtggatga tcatcacttt aaggtgatcc tgcactatgg cacactggta 300
atcgacgggg ttacgccgaa catgatcgac tatttcggac ggccgtatga aggcatcgcc 360
gtgttcgacg gcaaaaagat cactgtaaca gggaccctgt ggaacggcaa caaaattatc 420
gacgagcgcc tgatcaaccc cgacggctcc ctgctgttcc gagtaaccat caacggagtg 480
accggctggc ggctgtgcga acgcattctg gcgtaa 516

<210> SEQ ID NO 6
<211> LENGTH: 795
<212> TYPE: RNA
<213> ORGANISM: artificial
<220> FEATURE:
<223> OTHER INFORMATION: globin-leader + NanoLuc mRNA + poly(A)

<400> SEQUENCE: 6
gggagacaag cuugaauaca agcuacuugu ucuuuuugca ccuguacgga aguguuacuu 60

-continued cugcucuaaa agcugcggaa uuguaccccu agcguuuaaa cuuaagcuug gcaauccggu 120
acuguuggua aagccaccau ggucuucaca cucgaagauu ucguugggga cuggcgacag 180
acagccggcu acaaccugga ccaaguccuu gaacagggag gugugu ccag uuuguuucag 240 aaucucgggg uguccguaac uccgauccaa aggauugucc ugagcgguga aaaugggcug 300
aagaucgaca uccaugucau caucccguau gaaggucuga gcggcgacca aaugggccag 360
aucgaaaaaa uuuuuaaggu gguguacccu guggaugauc aucacuuuaa ggugauccug 420
cacuauggca cacugguaau cgacgggguu acgccgaaca ugaucgacua uuucggacgg 480
ccguaugaag gcaucgccgu guucgacggc aaaaagauca cuguaacagg gacccugugg 540
aacggcaaca aaauuaucga cgagcgccug aucaaccccg acggcucccu gcuguuccga 600
guaaccauca acggagugac cggcuggcgg cugugcgaac gcauucuggc guaaggccgc 660
gacucuagaa caacaacaau ugcauucauu uuauguuuca gguucagggg gaggugu ggg 720 agguuuuuuc ggauccucua gaggaucccc gggcgagcuc ccaaaaaaaa aaaaaaaaaa 780
aaaaaaaaaa aaccg 795

<210> SEQ ID NO 7
<211> LENGTH: 1209
<212> TYPE: DNA
<213> ORGANISM: human

<400> SEQUENCE: 7
atgctcgagg gagtgcaggt ggaaaccatc tccccaggag acgggcgcac cttccccaag 60
cgcggccaga cctgcgtggt gcactacacc gggatgcttg aagatggaaa gaaagttgat 120
tcctcccggg acagaaacaa gccctttaag tttatgctag gcaagcagga ggtgatccga 180
ggctgggaag aaggggttgc ccagatgagt gtgggtcaga gagccaaact gactatatct 240
ccagattatg cctatggtgc cactgggcac ccaggcatca tcccaccaca tgccactctc 300
gtcttcgatg tggagcttct aaaactggaa tctggcggtg gatccggagt cgacggattt 360
ggtgatgtcg gtgctcttga gagtttgagg ggaaatgcag atttggctta catcctgagc 420
atggagccct gtggccactg cctcattatc aacaatgtga acttctgccg tgagtccggg 480
ctccgcaccc gcactggctc caacatcgac tgtgagaagt tgcggcgtcg cttctcctcg 540
ctgcatttca tggtggaggt gaagggcgac ctgactgcca agaaaatggt gctggctttg 600
ctggagctgg cgcagcagga ccacggtgct ctggactgct gcgtggtggt cattctctct 660
cacggctgtc aggccagcca cctgcagttc ccaggggctg tctacggcac agatggatgc 720
cctgtgtcgg tcgagaagat tgtgaacatc ttcaatggga ccagctgccc cagcctggga 780
gggaagccca agctcttttt catccaggcc tgtggtgggg agcagaaaga ccatgggttt 840
gaggtggcct ccacttcccc tgaagacgag tcccctggca gtaaccccga gccagatgcc 900
accccgttcc aggaaggttt gaggaccttc gaccagctgg acgccatatc tagtttgccc 960
acacccagtg acatctttgt gtcctactct actttcccag gttttgtttc ctggagggac 1020
cccaagagtg gctcctggta cgttgagacc ctggacgaca tctttgagca gtgggctcac 1080

-continued

```
tctgaagacc tgcagtccct cctgcttagg gtcgctaatg ctgtttcggt gaaagggatt   1140

tataaacaga tgcctggttg ctttaatttc ctccggaaaa aacttttctt taaaacatca   1200

gctagctag                                                           1209


<210> SEQ ID NO 8
<211> LENGTH: 1383
<212> TYPE: RNA
<213> ORGANISM: artificial
<220> FEATURE:
<223> OTHER INFORMATION: globin-leader + iCaspase9 mRNA + poly(A)

<400> SEQUENCE: 8

gggagacaag cuugaauaca agcuacuugu ucuuuuugca ccuguacgga aguguuacuu     60

cugcucuaaa agcugcggaa uuguacccac uuaauacgac ucacuauagg cuagacugcc    120

augcucgagg gagugcaggu ggaaaccauc uccccaggag acgggcgcac cuuccccaag    180

cgcggccaga ccugcguggu gcacuacacc gggaugcuug aagauggaaa gaaaguugau    240

uccucccggg acagaaacaa gcccuuuaag uuuaugcuag gcaagcagga ggugauccga    300

ggcugggaag aaggggaugc ccagaugagu gugggucaga gagccaaacu gacuauaucu    360

ccagauuaug ccuauggugc cacugggcac ccaggcauca ucccaccaca ugccacucuc    420

gucuucgaug uggagcuucu aaaacuggaa ucuggcggug gauccggagu cgacggauuu    480

ggugaugucg gugcucuuga gaguuugagg ggaaaugcag auuuggcuua cauccugagc    540

auggagcccu guggccacug ccucauuauc aacaauguga acuucugccg ugaguccggg    600

cuccgcaccc gcacuggcuc caacaucgac ugugagaagu ugcggcgucg cuucuccucg    660

cugcauuuca ugguggaggu gaagggcgac cugacugcca agaaaauggu gcuggcuuug    720

cuggagcugg cgcagcagga ccacggugcu cuggacugcu gcgugguggu cauucucucu    780

cacggcuguc aggccagcca ccugcaguuc ccaggggcug ucuacggcac agauggaugc    840

ccugugucgg ucgagaagau ugugaacauc uucaauggga ccagcugccc cagccuggga    900

gggaagccca agcucuuuuu cauccaggcc uguggugggg agcagaaaga ccauggguuu    960

gagguggccu ccacuucccc ugaagacgag uccccuggca guaaccccga gccagaugcc   1020

accccguucc aggaagguuu gaggaccuuc gaccagcugg acgccauauc uaguuugccc   1080

acacccagug acaucuuugu guccuacucu acuuucccag guuuuguuuc cuggagggac   1140

cccaagagug gcuccuggua cguugagacc cuggacgaca ucuuugagca gugggcucac   1200

ucugaagacc ugcagucccu ccugcuuagg gucgcuaaug cuguuucggu gaaagggauu   1260

uauaaacaga ugccugguug cuuuaauuuc cuccggaaaa aacuuuucuu uaaaacauca   1320

gcuagcuaga ggaucccogg gcgagcuccc aaaaaaaaaa aaaaaaaaaa aaaaaaaaaa   1380

ccg                                                                 1383
```

COMPOSITION, LIPID PARTICLE MANUFACTURING KIT, SUBSTANCE DELIVERY METHOD, AND DETECTION METHOD

CROSS-REFERENCE TO RELATED APPLICATIONS

This application is a Continuation Application of PCT Application No. PCT/IB2020/058307, filed Sep. 7, 2020 and based upon and claiming the benefit of priority from Japanese Patent Application No. 2020-049219, filed Mar. 19, 2020, the entire contents of all of which are incorporated herein by reference.

SEQUENCE LISTING

The instant application contains a Sequence Listing which has been submitted electronically in ASCII format and is hereby incorporated by reference in its entirety. Said ASCII copy, created on Nov. 4, 2021, is named 539237US ST25.txt and is 7, 388 bytes in size.

FIELD

Embodiments described herein relate generally to a composition, a lipid particle manufacturing kit, a substance delivery method, and a detection method.

BACKGROUND

T-cell malignancy is a sort of malignant tumor disease including T-cell leukemia and T-cell lymphoma. There has been a standing need for delivery of therapeutic agent or diagnostic agent specifically to malignant tumor cells, for the purpose of treatment and diagnosis of various malignant tumors. For example, an antigen or a receptor specific to a predetermined malignant tumor cell is used in the delivery. T-cell malignant tumor cell has, however, a surface antigen almost indistinguishable from that of normal T cell, making difficult in treatment using the antigen or receptor.

DETAILED DESCRIPTION

In general, according to one embodiment, a composition is for delivering an objective substance to the T-cell malignant tumor cell. The composition contains a substance delivery carrier. The substance delivery carrier has a lipid particle, and the objective substance encapsulated in the lipid particle. The lipid particle contains, as constituents thereof, at least a first lipid represented by formula (I) and a second lipid represented by formula (II).

Embodiments will be described hereinafter with reference to the accompanying drawings. Note that, in these embodiments, substantially the same structural elements will be designated by the same reference symbols sign and the explanations therefor may be partly omitted. Further, the drawings are only schematic, and therefore, the relation between the thickness of each element and its planar dimension, the ratio in thickness between the elements and the like may be different from those of the actual cases.

First Embodiment

Lipid Particle

Figure 1:
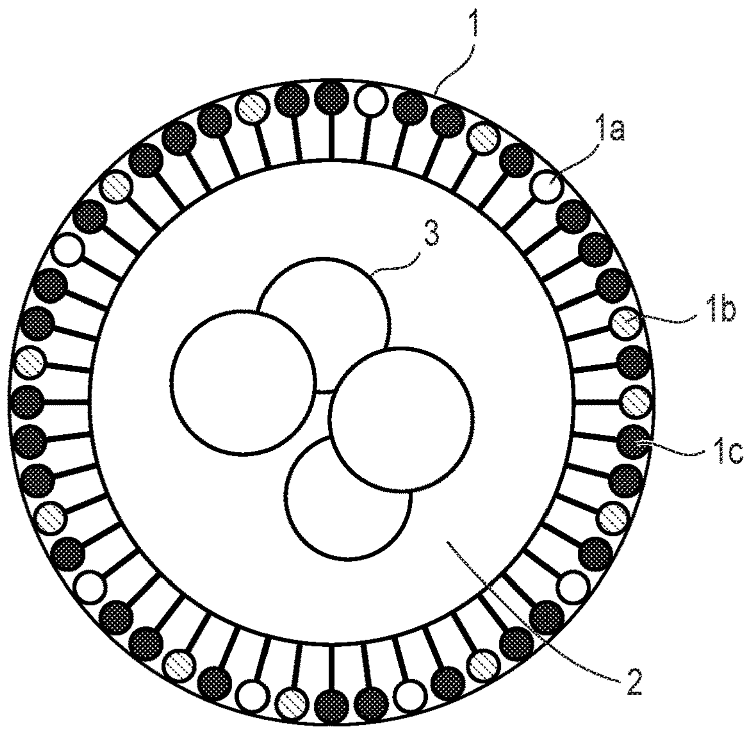
FIG. 1 is a cross sectional view showing an example of a lipid particle of a first embodiment.

According to a first embodiment, there is provided a lipid particle for introducing an objective substance into T-cell malignant tumor cell. As shown in FIG. 1, a lipid particle 1 is a substantially spherical hollow body, and can encapsulate an objective substance 3 in a center lumen 2 thereof.

The objective substance 3 is a substance intended to be delivered into T-cell malignant tumor cell. The objective substance 3 can be any substance as long as it can be encapsulated in the lipid particle 1, and may typically be nucleic acid, protein, peptide, other organic compounds, inorganic compounds, therapeutic agent or diagnostic agent for T-cell malignancy, and the like.

The lipid particle 1 may be composed of, for example, a lipid membrane formed by a plurality of lipid molecules which are the source materials and are arranged with the aid of noncovalent bond. The lipid particle 1 contains, as the constituents thereof, at least a first lipid 1*a* and a second lipid 1*b*. The first lipid 1*a* is a lipid compound represented by formula (I) below, meanwhile the second lipid 1*b* is a lipid compound represented by formula (II) below.

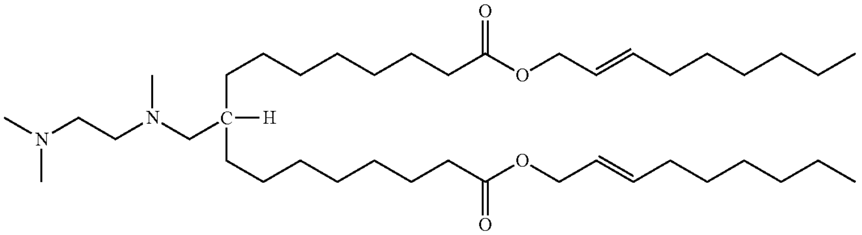

(I)

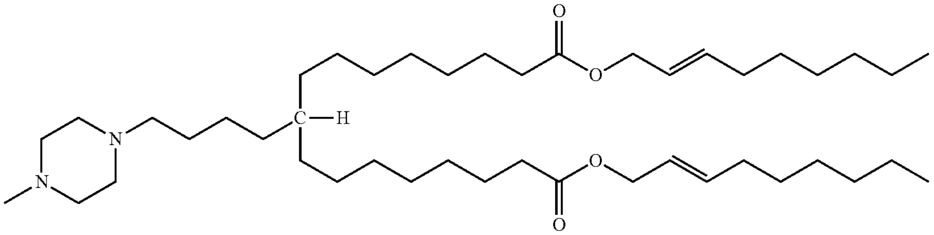

(II)

The lipid particle 1 may contain additional lipid, besides the first lipid 1*a* and the second lipid 1*b*. Of the composition of lipid molecule ingredients composing the lipid particle 1, a fraction composed of the first lipid 1*a* and the second lipid 1*b* will be referred to as a "first fraction", hereinafter. On the other hand, a fraction composed of lipid molecule ingredients other than the first lipid 1*a* and the second lipid 1*b* will be referred to as a "second fraction", hereinafter. Lipids contained in the second fraction will collectively be referred to as a "third lipid 1*c*", hereinafter.

The terms "first fraction" and "second fraction" merely indicate composition of the constituents of the lipid particle 1, and by no means imply physical location of the lipids contained therein. For example, the constituents of each of the first fraction and the second fraction are not necessarily gathered 10 independently in the lipid particle 1, instead the lipids contained in the first fraction and the lipids contained in the second fraction may exist in a mixed manner. Compounding ratio of the first fraction, relative to the whole lipid ingredients composing the lipid particle 1, preferably accounts for 30% or more and less than 50% (mole ratio).

Compounding ratio of the second lipid 1*b* in the first fraction is preferably 40% or more. In this case, efficiency of the objective substance 3 introduction and specificity to T-cell malignant tumor cell can be improved. With the compounding ratio of the second lipid 1*b* in the first fraction controlled to 50% or more, the amount of introduction into living body, that is, in vivo introduction of the objective substance 3 may be improved, which is more beneficial. The compounding ratio of the second lipid 1*b* is more preferably 60% or more. The upper limit of the compounding ratio of the second lipid 1*b* may be 80%, 90%, 95%, 96%, 97%, 98% or 99%.

Depending on the compounding ratio of the first lipid 1*a* and the second lipid 1*b* in the first fraction, size and cell permeability of the lipid particle 1 may be modified. For example, the more the second lipid 1*b*, the larger the size of lipid particle 1. Average size of the lipid particle 1 may be modified depending on intended use, and may typically be adjusted within the range from approximately 50 nm to approximately 300 nm. When intended for in vivo use for example, the average size may be adjusted within the range from approximately 70 nm to approximately 100 nm.

The lipid particle 1 may be incorporated by endocytosis into the T-cell malignant tumor cell, typically by bringing it into contact with the cell. The objective substance 3 can be then released into the cell. The lipid particle 1, having the first lipid 1*a* and the second lipid 1*b* contained therein, has the nature of being more easily incorporated by the T-cell malignant tumor cell, whereas being less easily incorporated in other cells such as normal blood cells. Hence, the objective substance 3 can be efficiently introduced into the T-cell malignant tumor cell, only by simply bringing the objective substance 3, preliminarily encapsulated in the lipid particle 1, into contact with the T-cell malignant tumor cell (for example by administration), without using an antigen or receptor having been used in the prior method. The lipid particle 1 can therefore be used for various uses that require selective or specific delivery of objective substance 3 to the T-cell malignant tumor cell.

Here, T-cell malignancy is a disease caused by malignant transformation of T cell (T lymphocyte). T-cell malignant tumor cell contains malignant T cells, such as T cell-derived leukemia cell, lymphoma cell and so forth.

Types of the third lipid 1*c* contained in the second fraction of the lipid particle 1 are not specifically limited, and the second fraction typically contains a base lipid. For example, a lipid, which is a major constituent of biological membrane, may be used as the base lipid. The base lipid is any of phospholipid or sphingolipid, such as diacylphosphatidylcholine, diacylphosphatidylethanolamine, ceramide, sphingomyelin, dihydrosphingomyelin, cephalin, cerebroside, and combinations of them.

For example, the base lipid may be preferably any of 1,2-dioleoyl-sn-glycero-3-phosphoethanolamine (DOPE), 1,2-stearoyl-sn-glycero-3-phosphoethanolamine (DSPE), 1,2-dipalmitoyl-sn-glycero-3-phosphatidylcholine (DPPC), 1-palmitoyl-2-oleoyl-sn-glycero-3-phosphatidylcholine (POPC), 1,2-di-O-octadecyl-3-trimethylammoniumpropane (DOTMA), 1,2-dioleoyl-3-dimethylammoniumpropane (DODAP), 1,2-dimyristoyl-3-dimethylammoniumpropane (14:0 DAP), 1,2-dipalmitoyl-3-dimethylammoniumpropane (16:0 DAP), 1,2-distearoyl-3-dimethylammoniumpropane (18:0 DAP), N-(4-carboxybenzyl)-N, N-dimethyl-2,3-bis (oleoyloxy)propane (DOBAQ), 1,2-dioleoyl-3-trimethylammoniumpropane (DOTAP), 1,2-dioleoyl-sn-glycero-3-phosphochlorine (DOPC), 1,2-dilinoleoyl-sn-glycero-3- phosphochlorine (DLPC), 1,2-dioleoyl-sn-glycero-3-phospho-L-serine (DOPS), cholesterol, and combinations of any of them.

Among the aforementioned base lipid, particularly preferred are lipids such as cationic lipid and neutral lipid, the content of which may be used for controlling acid dissociation constant of the lipid particle 1. DOTAP is preferably used as the cationic lipid, and DOPE is preferably used as the neutral lipid.

The second fraction also preferably contains a lipid capable of preventing the lipid particle 1 from aggregating. Such anti-aggregation lipid further preferably contains PEG (polyethylene glycol)-modified lipid such as polyethylene glycol (PEG) dimyristoylglycerol (DMG-PEG), polyamide oligomer derived from ω-amino (oligoethylene glycol)alkanoate monomer (U.S. Pat. No. 6,320,017 B), monosialoganglioside, or the like.

The second fraction may additionally contain any of lipid including relatively less toxic lipid for controlling toxicity; lipid having a functional group through which a ligand is bound to the lipid particle 1; and lipid for suppressing leakage of encapsulated substance, such as sterol, and more specifically cholesterol. Cholesterol is particularly preferably contained.

Types and composition of the lipids used for the second fraction are suitably selected, considering the acid dissociation constant (pKa) of the intended lipid particle 1, particle size of the lipid particle 1, type of the objective substance 3, intracellular stability, and so forth.

For example, when the second fraction contains DOPE, DOTAP, cholesterol and DMG-PEG, the lipid particle 1 will have particularly excellent delivery efficiency of the objective substance 3, and is therefore preferred.

Additional ingredient, besides the objective substance 3, may be encapsulated in the lipid particle 1 as necessary. The additional ingredient is typically pH adjustor, osmoregulator, gene activator, any of other remedies or diagnostic agents for T-cell malignant tumor cell, or the like. The pH adjustor is typically organic acid such as citric acid, or salt thereof. The osmoregulator is typically sugar or amino acid. The gene activator will be described later.

The lipid particle 1 that encapsulates the objective substance 3 and other optional substance may be manufactured, typically by any of known methods for encapsulating small molecules into lipid particle, such as the Bangham method, organic solvent extraction method, surfactant removal method, and freeze-thaw method. For example, a lipid mixture obtained by adding materials of the lipid particle 1 according to desired ratio into an organic solvent such as alcohol, and an aqueous buffer that contains ingredient to be encapsulated such as the objective substance 3 are prepared, and the aqueous buffer is then poured into the lipid mixture. The obtained mixture is stirred to be suspended, to thereby form the lipid particle 1 encapsulating the objective substance 3 or the like.

Compounding ratio of the ingredients of the lipid particle 1 is easily controllable by changing the mixing ratio of the individual materials in the lipid mixture. For example, the compounding ratio of the ingredients of the lipid particle 1 may be nearly equal to the mixing ratio of the individual materials in the lipid mixture. Ratio of amount of the substances to be encapsulated in the lipid particle 1 is easily controllable by changing the ratio of amount of the substances in the aqueous buffer.

The lipid particle 1 encapsulating the objective substance 3 will also be referred to as "substance delivery carrier", hereinafter.

Composition

The substance delivery carrier may be provided in the form of liquid composition contained in a suitable carrier. The carrier may typically be water, aqueous sodium chloride solution such as saline, aqueous glycine solution, buffer solution, or the like. The substance delivery carrier may alternatively be provided in the form of dry powdery composition. The powdery composition becomes ready to use by adding thereto proper liquid such as any of aforementioned carriers by user.

The composition may further contain a substance that improves storage stability, besides the substance delivery carrier. The substance that improves storage stability is exemplified by, but not specifically limited to, albumin, lipoprotein, apolipoprotein, glycoprotein such as globulin, etc.; pH adjustor, buffering agent, tonicity adjustor, etc.; pharmaceutically acceptable participant capable of assimilating the composition to the physiological state, such as sodium acetate, sodium lactate, sodium chloride, potassium chloride and calcium chloride; lipophilic free radical quencher such as α-tocopherol, capable of suppressing damage induced by free radical; and lipid protective agent such as water-soluble chelator represented by ferrioxamine, capable of suppressing peroxidative damage of lipid and of improving storage stability.

In a case where the substance delivery carrier is intended for administration to living body, the composition preferably has a pharmaceutically acceptable chemical composition, and is sterilized by any of known methods.

According to another embodiment, there is provided a lipid mixture used for manufacturing the lipid particle 1. The lipid mixture contains at least the first lipid 1*a* and the second lipid 1*b*. The lipid mixture can contain the first lipid 1*a* and the second lipid 1*b* which are mixed according to any of the aforementioned desired mixing ratios, and can contain lipid that belongs to the second fraction. The lipid mixture may be provided in the form of a kit for manufacturing the lipid particle 1, together with a desired objective substance 3.

Second Embodiment

In a second embodiment, exemplary usage of the lipid particle 1 for reducing or extinguishing the T-cell malignant tumor cell will be explained. In this case, a substance for reducing or extinguishing the T-cell malignant tumor cell can be used as the objective substance 3. An exemplary lipid particle 1 encapsulating such objective substance 3, that is, a substance delivery carrier 10, will be explained referring to FIG. 2.

Substance Delivery Carrier

Figure 2:
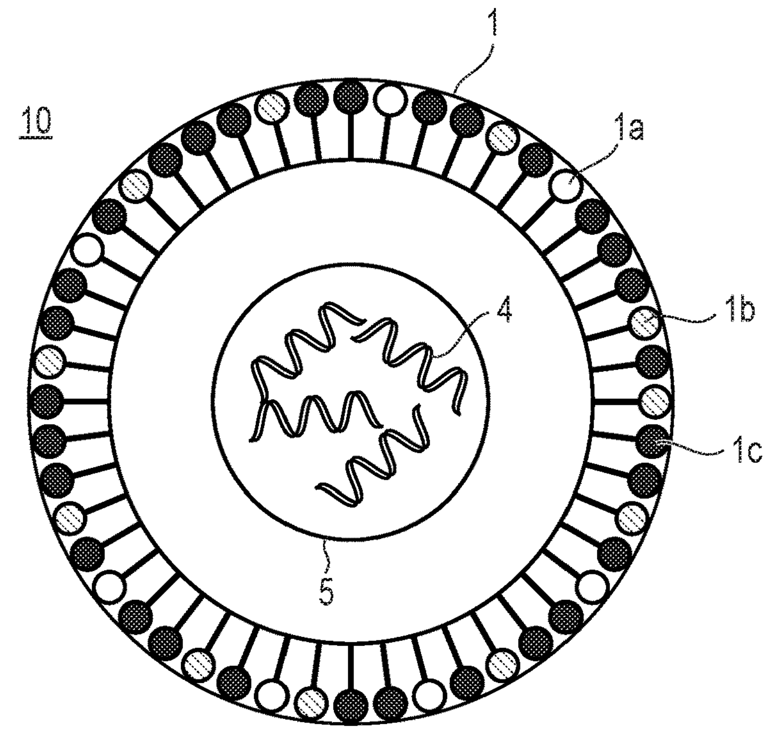
FIG. 2 is a cross sectional view showing an example of a substance delivery carrier of a second embodiment.

As shown in FIG. 2, the substance delivery carrier 10 has a lipid particle 1, and RNA4 encapsulated in the lipid particle 1 as objective substance 3. For example, RNA4 is encapsulated within the lipid particle 1, while being condensed with a nucleic acid condensing peptide 5.

The lipid particle 1 usable here may be any of lipid particles 1 explained in the first embodiment.

RNA4 is typically an RNA having an mRNA (messenger RNA) sequence of a cytocidal gene.

The term "cytocidal gene" described herein is a general term for group of genes that induce, for example, a cytocidal effect (mainly apoptosis) in human cells including cancer cells, and is also referred to as "suicide gene".

The cytocidal gene includes cancer suppressor genes (p53, Rb, ARF, etc.), death ligand receptor genes (Fas, Tumor-necrosis factor receptor (TNFR), Death receptor (DR) 4, DR5, etc.), apoptosis promotion genes (Bax, Bak, Bim, Bid, Bad, Noxa, Puma, etc.), apoptosis inhibition factor antagonist genes (Smac, DIABLO, etc.), caspase genes (Caspase 3, Caspase 6, Caspase 7, Caspase 9, Caspase 8, Caspase 10, inducible caspase 9 (iCaspase 9), etc.), virus-derived gene (HSV-tk gene), and the like.

mRNA of the cancer suppressor genes may either be Pre-mRNA before being spliced, or matured mRNA after being spliced. RNA4 may alternatively be an mRNA of a cytocidal gene modified after transcription, which may be added CAP on the 5' terminal, and polyadenylated at the 3' terminal.

RNA4 may contain an additional sequence, besides the mRNA sequence of the cytocidal gene. Such additional sequence is for enhancing efficiency of transcription and expression, and is exemplified by globin leader sequence bound to the 5' terminal and/or poly (A) sequence bound to the 3' terminal.

RNA4 is preferably modified to have decomposition-resistant. Such modification may be any of known modifications that make RNA insusceptible to decomposition by RNase or the like, and is exemplified by use or introduction of natural modified nucleotide or unnatural nucleotide to RNA, use or addition of unnatural sequence, addition of natural or unnatural CAP structure, or the like.

The natural modified nucleotide is exemplified by pseudouridine, 5-methylcytidine, 1-methyladenosine, and the like. The unnatural nucleotide is exemplified by BNA (bridged nucleic acid), LNA (locked nucleic acid), PNA (peptide nucleic acid), and the like.

The unnatural sequence is typically an artificially synthesized, non-naturally-occurring base sequence, and is exemplified by random base sequence, and hybrid sequence of natural or unnatural amino acid and nucleic acid. The unnatural sequence is preferably bound, for example, to the terminal of RNA.

The natural CAP structure is exemplified by CAP0 (m7GpppN), CAP1 (m7GpppNm), and the like. The unnatural CAP structure is exemplified by ARCA (Anti-Reverse Cap Analog), LNA-guanosine, or the like. The unnatural CAP structure is preferably bound, for example, to the 5' terminal of RNA.

One to approximately 1000 molecules of RNA4 are preferably contained in the lipid particle 1.

RNA4 may be encapsulated in the lipid particle 1, in its intact form, or after being condensed with the nucleic acid condensing peptide 5. Use of the nucleic acid condensing peptide 5 can condense nucleic acid in a compact size, making it possible to encapsulate larger amount of RNA4 in the lipid particle 1 with a smaller size. This also makes it possible to reduce the amount of RNA4 that remains outside the lipid particle 1, and to prevent the substance delivery carriers 10 from aggregating with each other. Delivery efficiency of RNA4 may thus be enhanced.

The nucleic acid condensing peptide 5 is preferably a peptide that contains cationic amino acid, which accounts for 45% or more of the whole. More preferred nucleic acid condensing peptide 5 has sequence RRRRRR (first amino acid sequence) (residues 16-21 of SEQ ID NO: 1) at one terminal, and has sequence RQRQR (second amino acid sequence) (residues 1-5 of SEQ ID NO: 1) at the other terminal. Between the first amino acid sequence and the second amino acid sequence, there is no or one or more intermediate sequences composed of RRRRRR (residues 16-21 of SEQ ID NO: 1 or RQRQR (residues 1-5 of SEQ ID NO: 1). Between two adjacent sequences among the first amino acid sequence, the second amino acid sequence and the intermediate sequence, there are contained two or more neutral amino acids. The neutral amino acid is typically G or Y. Alternatively, the other terminal may have RRRRRR (first amino acid sequence) (residues 16-21 of SEQ ID NO: 1, in place of the second amino acid sequence.

The nucleic acid condensing peptide 5 preferably has amino acid sequences below:

```
                                    (SEQ ID NO: 1)
RQRQRYYRQRQRGGRRRRRR

                                    (SEQ ID NO: 2)
RQRQRGGRRRRRR

                                   (SEQ ID NO: 3)
RRRRRRYYRQRQRGGRRRRRR.
```

Further, the nucleic acid condensing peptide 5 having an amino acid sequence below may be used in combination with any of the aforementioned nucleic acid condensing peptide 5. This peptide can further condense the nucleic acid aggregate having been condensed with the aforementioned nucleic acid condensing peptide 5.

```
                                    (SEQ ID NO: 4)
GNQSSNFGPMKGGNFGGRSSGPYGGGGQYFAKPRNQGGY (M9)
```

RNA4 may be condensed, for example, by mixing RNA4 with the nucleic acid condensing peptide 5 under stirring, before being encapsulated into the lipid particle 1.

Considering demonstration of the aforementioned effects, the nucleic acid condensing peptide 5 is preferably used in a case where the objective substance 3 is a nucleic acid such as RNA4, but the nucleic acid condensing peptide 5 is not always necessarily used depending on types of the objective substance 3 to be used.

Besides RNA4, optional pH adjustor, osmoregulator, gene activator, other therapeutic agent for T-cell malignant tumor cell and so forth may further encapsulated in the lipid particle 1.

The gene activator is a reagent that promotes or induces cytocidal action cause by expression of RNA4 and/or expressed factor. For example, in a case where RNA4 encodes iCaspase 9 gene, a chemical inducer of dimerization (CID) is preferably encapsulated as the gene activator together therewith.

Substance Delivery Method

Figure 3:
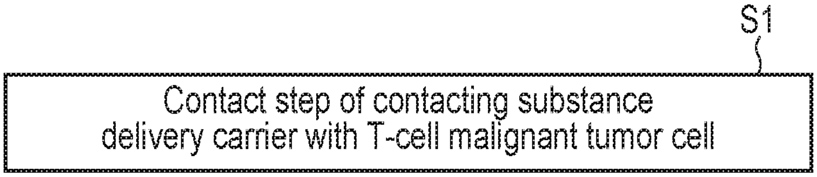
FIG. 3 is a flow chart showing an example of substance delivery method of the second embodiment.

A substance delivery method using the substance delivery carrier 10 of the second embodiment will be explained below. The substance delivery method includes, as shown in FIG. 3, contacting the substance delivery carrier 10 of the embodiment, with the T-cell malignant tumor cell (contact step S1).

T-cell malignant tumor cell typically exists in vivo in a subject. The subject is preferably human, but may be any of animals other than human. The animals are preferably mammals. The subject may be the one having already been diagnosed to have T-cell malignancy, or may be the one having been suffered from, or suspected of T-cell malignancy.

The contact step S1 in this case is carried out by administering the composition that contains the substance delivery carrier 10 to the subject. Route of administration is not specifically limited, so that the administration is carried out systemically for example by intravenous injection, subcutaneous injection, intramuscular injection, arterial injection, epidural injection, cerebrospinal cavity injection, intrathoracic injection, intraperitoneal injection, local intralesional injection, or drip. Administration schedule may only be selectable considering for example purpose; and sex, age, body weight and pathological condition of the subject. In addition, it may be single administration, or may be repetitive or periodical multiple administration. Upon being administered, the substance delivery carrier 10 is conveyed typically by the blood, and brought into contact in vivo with a T-cell malignant tumor cell 6.

The composition of the lipid particle 1 of the substance delivery carrier 10 in this case is preferably determined to adjust the particle size of the lipid particle 1 to 100 μm or smaller. The compounding ratio of the second lipid 1*b* in the first fraction is preferably 50% or more. The compounding ratio is more preferably 60% or more.

Figure 4:
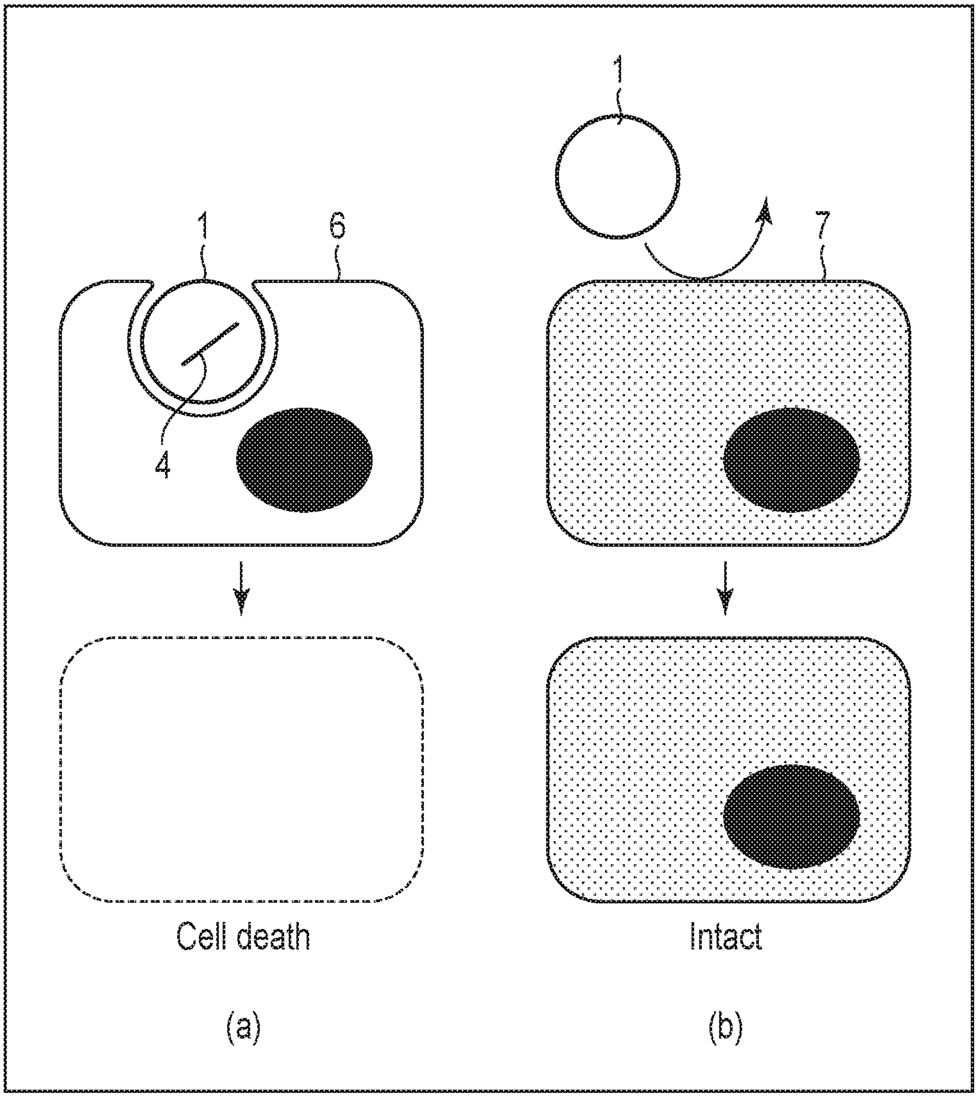
FIG. 4 is a schematic view showing an example of substance delivery method of the second embodiment.

As shown in FIG. 4 part (a), the substance delivery carrier 10 which is brought into contact with the T-cell malignant tumor cell 6 is then incorporated for example by endocytosis into the T-cell malignant tumor cell 6. Although not shown in FIG. 4 part (a), RNA4 is therefore introduced into the T-cell malignant tumor cell 6, RNA4 is then transcribed within the T-cell malignant tumor cell 6, and thereby a cytocidal factor is expressed. The cytocidal factor then goes into a cascade mechanism or signal transmission, depending on its type, to induce cell death of the T-cell malignant tumor cell 6. Alternatively, in some cases, depending on type of the cytocidal gene, the T-cell malignant tumor cell 6 may be suppressed from further proliferating. Consequently, the T-cell malignant tumor cell 6 in the subject may be reduced or extinguished.

On the other hand, as shown in FIG. 4 part (b), the substance delivery carrier 10 is less likely to be incorporated into other cell 7, such as normal blood cell or the like, leaving such other cell 7 alive (intact) and proving safety.

Considering the above, according to the substance delivery carrier and the substance delivery method according to the second embodiment, it becomes possible to deliver RNA4 to the T-cell malignant tumor cell 6 of the subject efficiently, and to reduce or extinguish the T-cell malignant tumor cell. The T-cell malignancy can therefore be treated in an efficient and safe manner.

Since the substance delivery carrier 10, which introduces the cytocidal gene in the form of RNA4, can more rapidly and efficiently express the cytocidal factor, as compared with the case where it is introduced in the form of DNA, since a transcription step is omitted. Further, the size of lipid particle 1 can be reduced as compared with the case where the cytocidal factor is introduced in the form of protein, which improves efficiency of introduction and makes the manufacture easier since there is no need to change agent to be encapsulated into the lipid particle 1 depending on the types of cytocidal factor.

However, the cytocidal gene is not limited to the form of mRNA, instead may alternatively be in the form of DNA or protein. Again alternatively, the lipid particle 1 may be used for reducing or extinguishing the T-cell malignant tumor cell 6, using other therapeutic agent in place of the cytocidal gene.

In another embodiment, the substance delivery carrier 10 and the substance delivery method of the second embodiment may also be used for reducing or extinguishing in vitro T-cell malignant tumor cell 6. The T-cell malignant tumor cell 6 in this case may typically be a cell taken out from a living body and cultured, or a cell established as a cell line. The contact step S1 in this case may be carried out typically by dropping the composition containing the lipid particle 1 onto the cell.

Third Embodiment

In a third embodiment, exemplary usage of the lipid particle 1 for detecting the T-cell malignant tumor cell will be explained. In this case, a substance for detecting the T-cell malignant tumor cell may be used as the objective substance 3.

Figure 5:
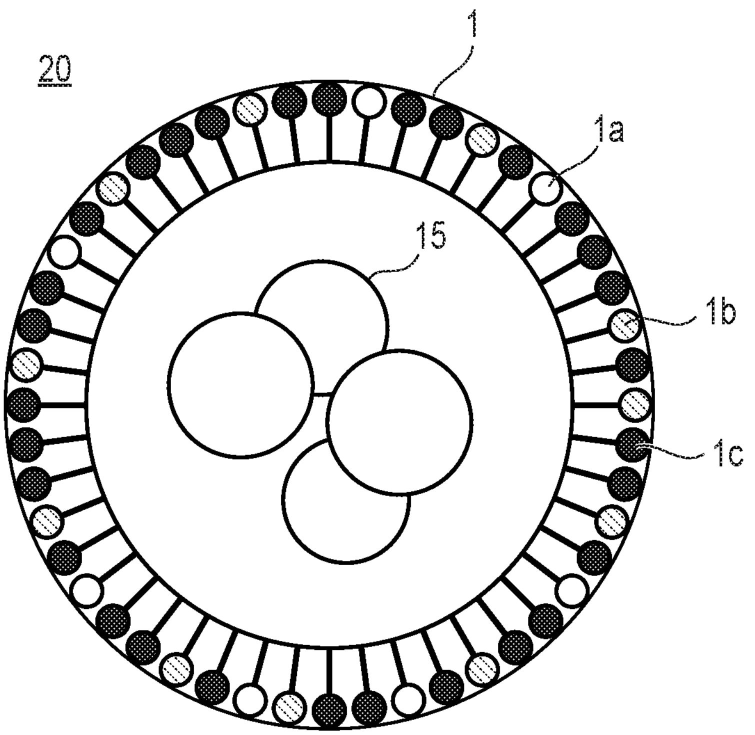
FIG. 5 is a cross sectional view showing an example of a substance delivery carrier of a third embodiment.

As shown in FIG. 5, a substance delivery carrier 20 of the third embodiment contains a diagnostic agent 15 as the objective substance 3, in place of RNA4 in the second embodiment. Lipid particle 1 used here may be any of those explained in the first embodiment.

For example, the diagnostic agent 15 may be a substance capable of generating a detectable first signal. The diagnostic agent 15 may be a substance that can be encapsulated into the lipid particle 1. A substance that can generate an optical first signal or a substance that contains a radioisotope detectable by a nuclear medical diagnostic apparatus can be used as the diagnostic agent 15. When the substance delivery carrier 20 is for in vivo administration, it is preferable to select a pharmaceutically acceptable substance as the diagnostic agent 15.

Besides the diagnostic agent 15, optional pH adjustor, osmoregulator, gene activator, other diagnostic agent for T-cell malignant tumor cell and so forth may be encapsulated the lipid particle 1.

Substance Delivery Method

Figure 6:
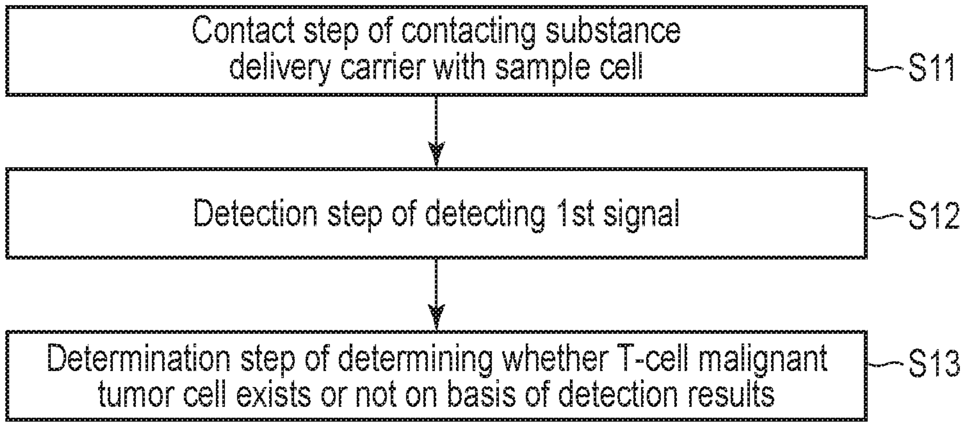
FIG. 6 is a flow chart showing an example of detection method of the third embodiment.

A substance delivery method for detecting the T-cell malignant tumor cell is explained below, by delivering the diagnostic agent 15 to the T-cell malignant tumor cell, using the substance delivery carrier 20 of the third embodiment. As shown in FIG. 6, the substance delivery method of the third embodiment includes: contacting the lipid particle 1 that encapsulates the diagnostic agent 15 (substance delivery carrier 20) with a sample cell (contact step S11); detecting the first signal (detection step S12); and determining presence or absence of the T-cell malignant tumor cell in the sample cell, on the basis of result of the detection (determination step S13).

The sample cell is a cell group suspected or predicted to contain the T-cell malignant tumor cell 6. The sample cell may typically be a cell having been diagnosed to be the T-cell malignancy, or may be a cell that exists in vivo in a subject suspected to be affected by T-cell malignancy, or may be a cell group taken out from the living body of these subject. The sample cell may alternatively be a cell group obtained by artificial differentiation or malignant transformation.

In the case where the sample cell that exists in vivo is used, the contact step S11 is carried out by administering the composition that contains the substance delivery carrier 20 to the subject. In the case where the sample cell that exist in vitro is used, the contact step S1 is carried out typically by dropping the composition that contains the substance delivery carrier 20 to the sample cell.

Figure 7:
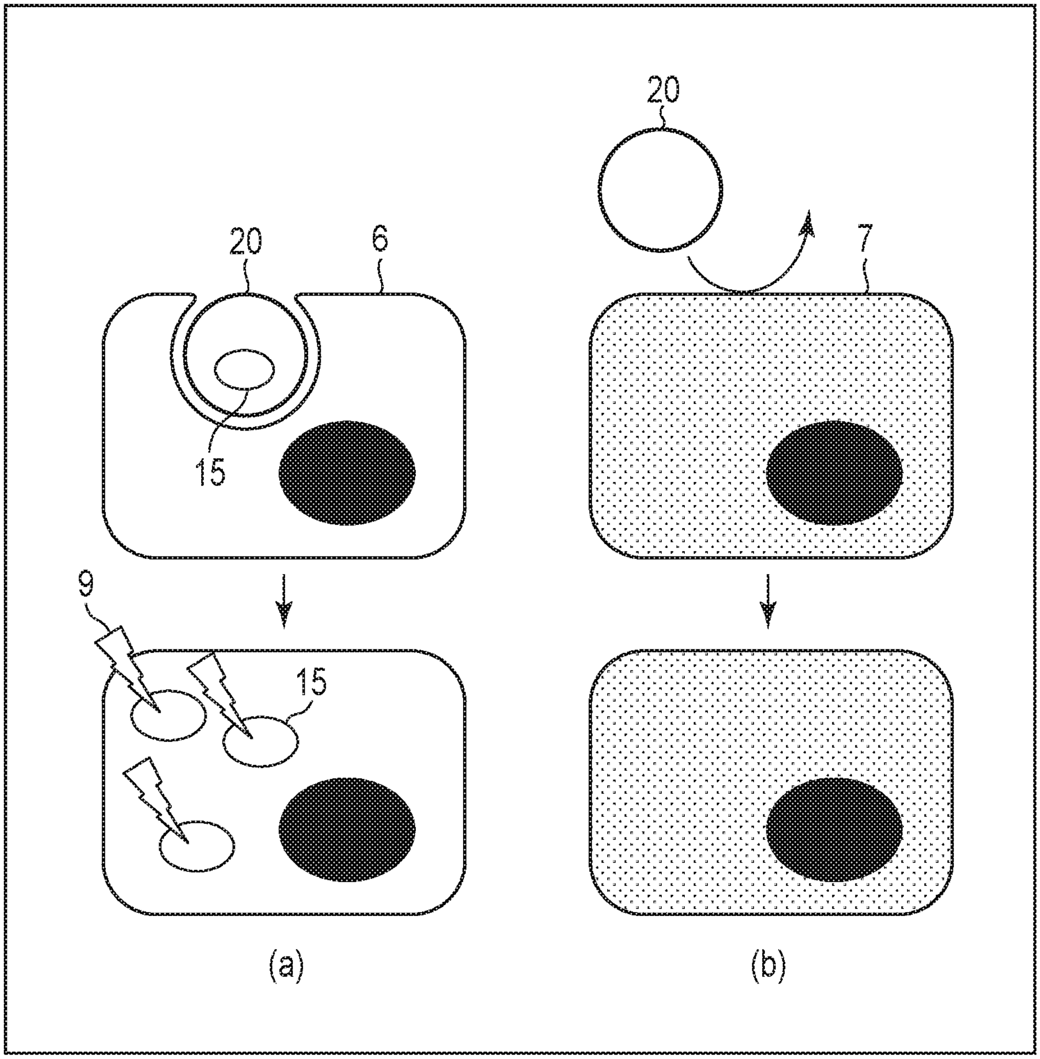
FIG. 7 is a schematic view showing an example of detection method of the third embodiment.

As shown in FIG. 7 part (a), the substance delivery carrier 20, brought into contact with the T-cell malignant tumor cell 6, is then incorporated into the T-cell malignant tumor cell 6. In this way, the diagnostic agent 15 is incorporated into the T-cell malignant tumor cell 6.

In detection step S12, the first signal is detected. A first signal 9 is detected using an appropriate device suited to the type of the diagnostic agent 15. Any of known in vivo imaging methods can be used in a case where the substance delivery carrier 20 is administered in vivo. Fluorescence molecular tomography (FMT) or the like can be used in a case where the first signal 9 is fluorescence. In a case where the sample cell is an in vitro cell, the detection may be carried out by a microscope, optical sensor or the like. For an exemplary case where the diagnostic agent 15 is a radioisotope, the detection may be carried out by a nuclear medical diagnostic apparatus or the like.

On the other hand, as shown in FIG. 7 part (b), the substance delivery carrier 20 is less likely to be incorporated into other cell 7, so that the first signal 9 is not obtained from such other cell 7.

Next, whether the T-cell malignant tumor cell exists in the sample cell or not is determined, using the detection results (determination step S13). For example, if a cell from which the first signal 9 is obtained is exists, the sample cell may be determined to have the T-cell malignant tumor cell. In a case where the sample cell is a cell group derived from the subject, information on the determination results obtained in the determination step S13 may be used, for example, to diagnose whether the subject has the T-cell malignant tumor cell or not. Alternatively, the information on the determination results may be used to assist such diagnosis.

In another embodiment, the diagnostic agent 15 may be RNA that contains mRNA of a reporter gene. For example, the reporter gene is a gene coding a reporter protein. The reporter protein is a protein that generates a detectable first signal. The reporter protein is preferably less cytotoxic, and whose signal is detectable from a living cell.

The reporter protein is preferably selected for example from fluorescent proteins such as green fluorescent protein, red fluorescent protein and blue fluorescent protein; luminescent enzyme protein such as firefly luciferase, renilla luciferase, and NanoLuc (registered trademark) luciferase; reactive oxygen producing enzyme such as xanthine oxidase or nitrogen monoxide synthase; and chromogenic enzyme proteins such as β-galactosidase or chloramphenicol acetyltransferase.

In the same way as in the second embodiment, the RNA may further contain an additional sequence besides the mRNA of the reporter gene, may be modified to have decomposition resistant, or may be encapsulated within the lipid particle 1 while being condensed with the nucleic acid condensing peptide 5.

The lipid particle 1 according to the third embodiment may further encapsulate a gene activator that assists expression of the reporter protein from the mRNA of the reporter gene and/or generation of the first signal from the reporter protein.

According to the aforementioned substance delivery carrier and the detection method of the third embodiment, it now becomes possible to deliver the diagnostic agent 15 to the T-cell malignant tumor cell efficiently, and to detect and diagnose T-cell malignancy.

EXAMPLE

Examples of manufacture and usage of the substance delivery carrier of the embodiment will be explained below.

Example 1

Evaluation of Amount of Incorporation of Lipid Particle into T-cell Malignancy, Normal Blood Cell, Breast Cancer Cell, and Brain Tumor Cell Preparation of Lipid Particle A solution containing mRNA of green fluorescent protein (GFP) (from Jena Bioscience GmbH), and lipid solutions in ethanol were prepared. Compositions of the lipid solutions in ethanol are summarized in Table 1.

TABLE 1

| Composition of Lipid Solution in Ethanol (unit: mol) | | | | | | |
|---|---|---|---|---|---|---|
| | First fraction | | Second fraction | | | |
| | FFT-10 | FFT-20 | DOTAP | DOPE | Cholesterol | DMG-PEG |
| FFT-10/20 | 35 | 70.2 | 9.4 | 21 | 88.5 | 9.4 |
| FFT-10 (only) | 74 | 0 | 10.5 | 21 | 120 | 8 |
| FFT-20 (only) | 0 | 74 | 10.5 | 21 | 120 | 8 |

In the Table 1, "FFT-10" stands for a compound represented by formula (I), and "FFT-20" stand for a compound represented by formula (II).

(I)

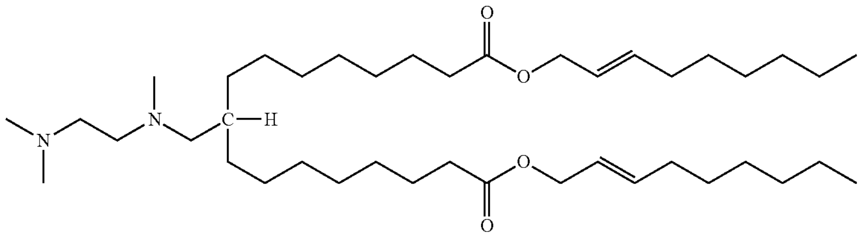

(II)

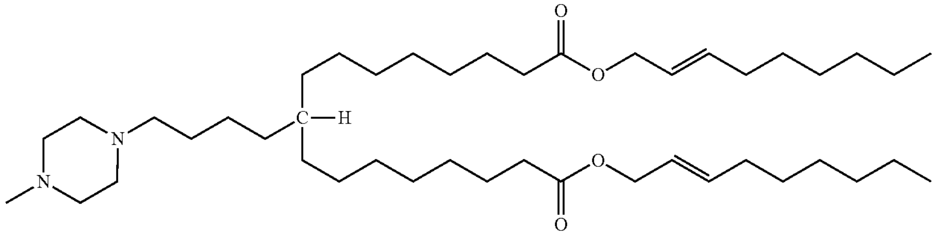

To each of the lipid solutions in ethanol summarized in Table 1, 0.4 mol of rhodamine-PE (registered trademark, from Avanti Polar Lipid, Inc.) was added, to which the solution containing GFP mRNA was added, and the content was thoroughly suspended by pipetting. To the solution, added was 7 times as much of a 10 mM HEPES buffer (pH7.3), and the solution was then condensed and replaced with the 10 mM HEPES buffer (pH7.3) using a centrifugal ultrafilter device (Amicon™ Ultra-0.5 mL, Ultracel-50K, from Millipore), to thereby obtain lipid particle that encapsulates GFP mRNA. The amount of mRNA encapsulated in the lipid particle was measured using an RNA quantitation system QuantiFluor™ RNA (from Promega Corporation).

Preparation of Cells

T-cell malignant tumor cell used here was a human leukemia cell line: Jurkat cell (from ATCC (registered trademark)). The normal blood cell used here was a human peripheral blood mononuclear cell: PBMC (from Lonza KK.). The breast cancer cell used here was a human mammary gland tumor cell line: MDA-MB-231 cell (from ATCC (registered trademark)), and the brain tumor cell used here was a human glioblastoma cell line: T98G cell (from ATCC (registered trademark)).

Introduction of mRNA Using Lipid Particle

Jurkat and PBMC were seeded on a 48-well culture plate at $5.0\times10^5$ cells/500 μL of TexMACS™ medium (from Miltenyi Biotec). On a 48-well culture plate, MDA-MD-231 was seeded using DMEM medium (containing 10% FBS, Gibco (registered trademark)) at 1.0×100 cells/250 μL, and T98G was seeded using RPMI1640 medium (containing 10% FBS, Gibco (registered trademark)) at $1.0\times10^5$ cells/250 μL. Then 1.0 μg of the lipid particle encapsulating GFP mRNA was added to Jurkat and PBMC, and 0.5 μg was added to MDA-MD-231 and T98G. Each mixture was thoroughly mixed by pipetting, and then cultured in an incubator with a conditioned atmosphere of 37° C. and 5% $CO_2$.

After 24 hours of the addition of the lipid particle to the cells, the cells were collected, and rhodamine fluorescence of the cells was measured using a fluorescence-activated cell sorter: FACS (FACSVerse™, from BD Biosciences). The amount of incorporation of lipid particle into the cells was measured, using rhodamine fluorescence of the cells as an index.

Results

Figure 8:
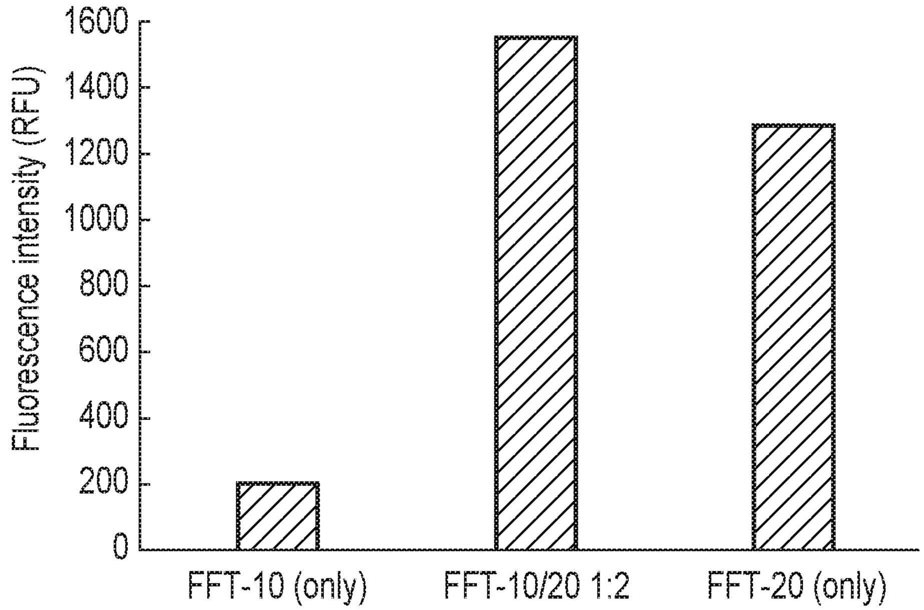
FIG. 8 is a graph showing experimental results of Example 1.

FIG. 8 shows fluorescence intensity of rhodamine in the T-cell malignant tumor cell. The fluorescence intensity was approximately 200 RFU for the case with FFT-10 (only), approximately 1300 RFU for the case with FFT-20 (only), and approximately 1600 RFU for the case with both of FFT-10 and FFT-20.

Figure 9:
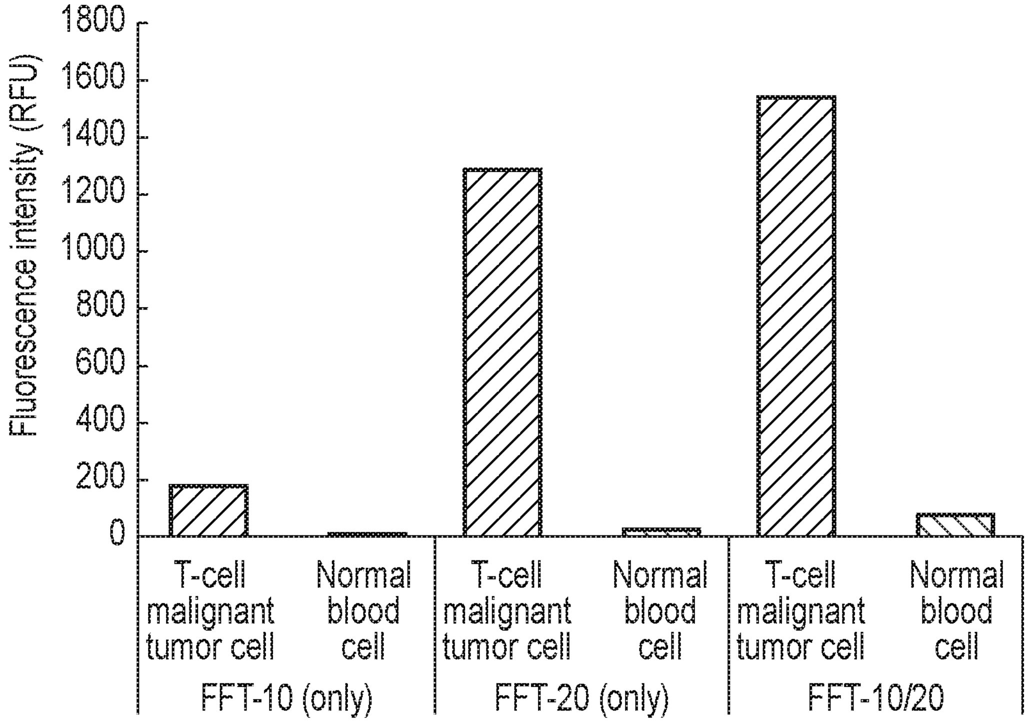
FIG. 9 is a graph showing experimental results of Example 1.

FIG. 9 shows fluorescence intensity of rhodamine compared between the T-cell malignant tumor cell and PBMC. The fluorescence intensity, in the case with FFT-10 (only), was approximately 200 RFU for the T-cell malignant tumor cell (Jurkat), and approximately 10 RFU for PBMC. The fluorescence intensity, in the case with FFT-20 (only), was approximately 1300 RFU for T-cell malignant tumor cell, and approximately 25 RFU for PBMC. The fluorescence intensity, in the case with both of FFT-10 and FFT-20, was approximately 1600 RFU for the T-cell malignant tumor cell, and approximately 100 RFU for PBMC.

All cases demonstrated that larger amount of liposome, encapsulating mRNA, was incorporated in the T-cell malignant tumor cell, than in PBMC. The difference was particularly distinctive for the case with FFT-20 (only), and for the case with both of FFT-10 and FFT-20. It was also found that the case with both of FFT-10 and FFT-20 demonstrated the largest amount of incorporation of liposome encapsulating mRNA.

Figure 10:
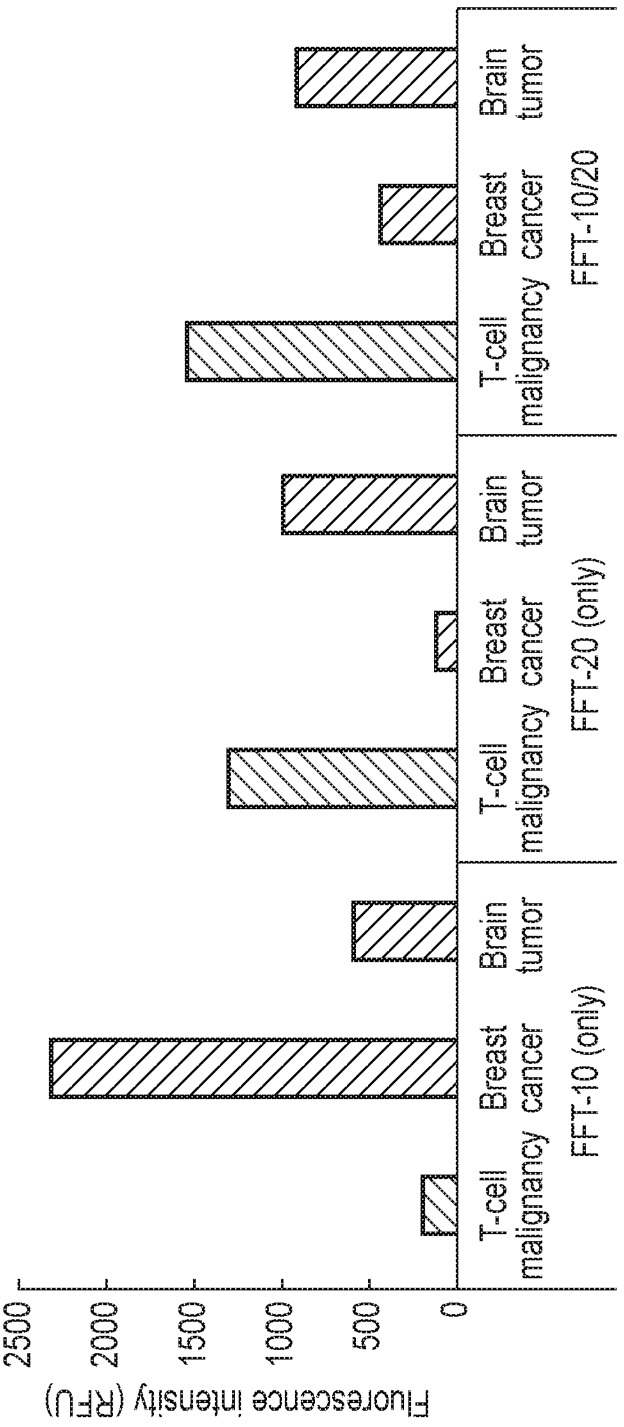
FIG. 10 is a graph showing experimental results of Example 1.

FIG. 10 shows results compared among the T-cell malignant tumor cell, the breast cancer cell, and the brain tumor cell. The fluorescence intensity of rhodamine, in the case with FFT-10 (only), was approximately 200 RFU for the T-cell malignant tumor cell (Jurkat), approximately 2300 RFU for the breast cancer cell (MDA-MB-231), and approximately 600 RFU for the brain tumor cell (T98G). The fluorescence intensity, in the case with FFT-20 (only), was approximately 1300 RFU for T-cell malignant tumor cell, approximately 100 RFU for the breast cancer cell, and approximately 1000 RFU for the brain tumor cell. The fluorescence intensity, in the case with both of FFT-10 and FFT-20, was approximately 1600 RFU for the T-cell malignant tumor cell, approximately 500 RFU for the breast cancer cell, and approximately 1000 RFU for brain tumor cell.

The cases with FFT-20 (only), and with both of FFT-10 and FFT-20 suggested that larger amount of liposome, encapsulating mRNA, was incorporated in the T-cell malignant tumor cell, than in the breast cancer cell and the brain tumor cell. With FFT-10 (only), the amount of incorporation was largest in the breast cancer cell.

The results shown in FIGS. 9 and 10 indicate that, for the cases with FFT-20 (only), and with both of FFT-10 and FFT-20, larger amount of mRNA could be incorporated into the T-cell malignant tumor cell. Hence, in the next experiment, the lipid particles that contain FFT-20 (only), and both of FFT-10 and FFT-20, were further evaluated.

Example 2

Evaluation of Amount of Incorporation of Lipid Particle into T-Cell Malignant Tumor Cell and PBMC Preparation of Lipid Particle Lipid solutions in ethanol, containing rhodamine-PE (registered trademark, from Avanti Polar Lipid, Inc.) and lipids were prepared. Chemical compositions of the lipid solutions in ethanol are summarized in Table 2.

TABLE 2

| | Composition of Lipid Solution (Unit: mol) | | | | | |
|---|---|---|---|---|---|---|
| | First fraction | | Second fraction | | | |
| | FFT-10 | FF7-20 | DOTAP | DOPE | Cholesterol | DMG-PEG |
| No. 43 | 0 | 74 | 21 | 10.5 | 120 | 8 |
| No. 78 | 58.5 | 25.7 | 14 | 25.7 | 100.2 | 9.4 |
| No. 79 | 35 | 70.2 | 9.4 | 21 | 88.5 | 9.4 |
| No. 80 | 35 | 70.2 | 21 | 9.4 | 88.5 | 9.4 |

To each of the thus prepared lipid solutions in ethanol listed in Table 2, a solution containing luciferase mRNA (from Jena Bioscience GmbH) was added, and then thoroughly suspended by pipetting. To the solution, 7 times as much of a 10 mM HEPES buffer (pH7.3) was add, and the solution was then condensed and replaced with the 10 mM HEPES buffer (pH7.3) using a centrifugal ultrafilter device (Amicon™ Ultra-0.5 mL, Ultracel-50K, from Millipore), to thereby obtain each lipid particle that encapsulates the mRNA. The amount of mRNA encapsulated in the lipid particle was measured using an RNA quantitation system named QuantiFluor™ RNA (from Promega Corporation).

Preparation of Cells

The T-cell malignant tumor cell and PBMC, same as those used in Example 1, were used.

PBMC and Jurkat were seeded on a 48-well culture plate that contains at $5.0\times10^5$ cells/500 μL of TexMACS™ medium (from Miltenyi Biotec). After seeding, 2.0 μg of each lipid particle encapsulating the luciferase mRNA was added, the content was thoroughly mixed by pipetting, and then cultured in an incubator with a conditioned atmosphere of 37° C. and 5% $CO_2$. Twenty-four hours after, the culture plate was taken out, the cells were collected, and incorporation of the lipid particles into the cells, and expression of mRNA encapsulated in the lipid particles were examined.

The amount of incorporation of lipid particle into the cells was measured, using rhodamine fluorescence of the cells as an index. The rhodamine fluorescence of the cells was measured using a fluorescence-activated cell sorter: FACS (FACSVerse™, from BD Biosciences). The amount of expression of the luciferase mRNA encapsulated in the lipid particles was measured using luciferase luminescence intensity of the cells as an index. The luciferase luminescence intensity was measured using ONE-Glo™ Luciferase Assay System (from Promega Corporation), and a luminometer: Infinite (registered trademark) 200 PRO (from Tecan).

Results

Figure 11:
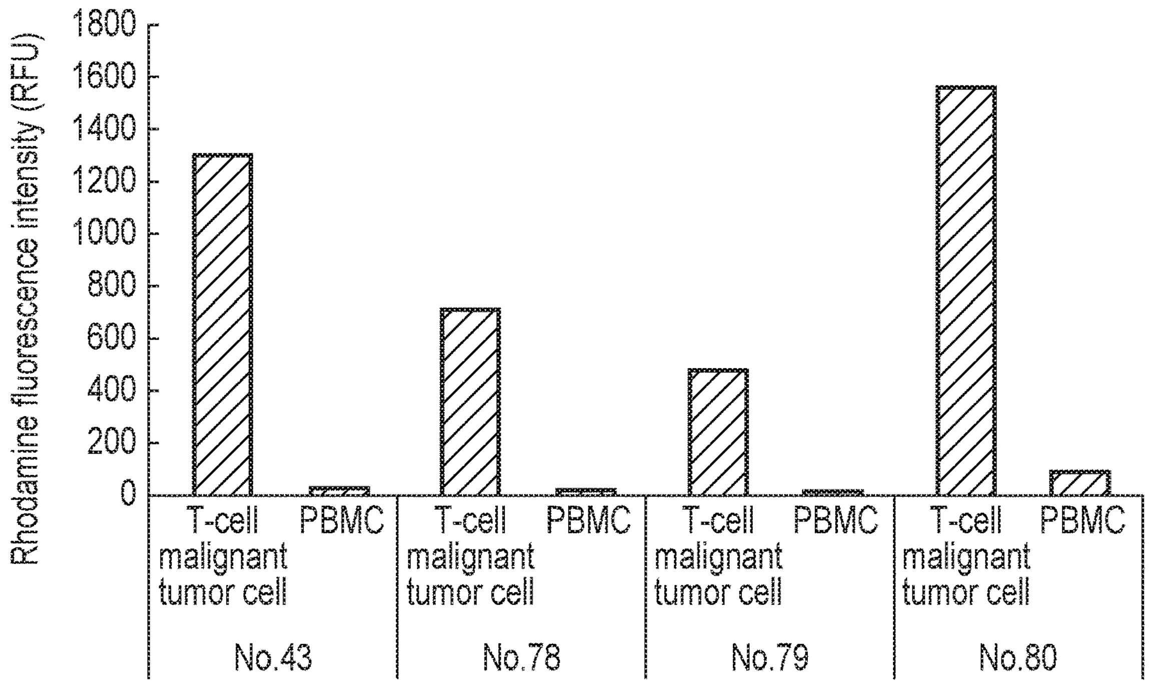
FIG. 11 is a graph showing experimental results of Example 2.

Measured results of the amount of rhodamine fluorescence are shown in FIG. 11. The fluorescence intensity, in the case of No. 43 (FFT-20 (only)), was approximately 1300 RFU for the T-cell malignant tumor cell (Jurkat), and approximately 25 RFU for PBMC. The fluorescence intensity, in the case of No. 78, was approximately 700 RFU for T-cell malignant tumor cell, and approximately 20 RFU for PBMC. The fluorescence intensity, in the case of No. 79, was approximately 500 RFU for T-cell malignant tumor cell, and approximately 15 RFU for PBMC. The fluorescence intensity, in the case of No. 80, was approximately 1500 RFU for T-cell malignant tumor cell, and approximately 10 RFU for PBMC.

All lipid particles were found that larger amounts thereof were incorporated into the T-cell malignant tumor cell, than in PBMC. In particular, No. 43 and No. 79 showed large differences in the amounts of incorporation easiness between two types of cell, proving their good performances.

Figure 12:
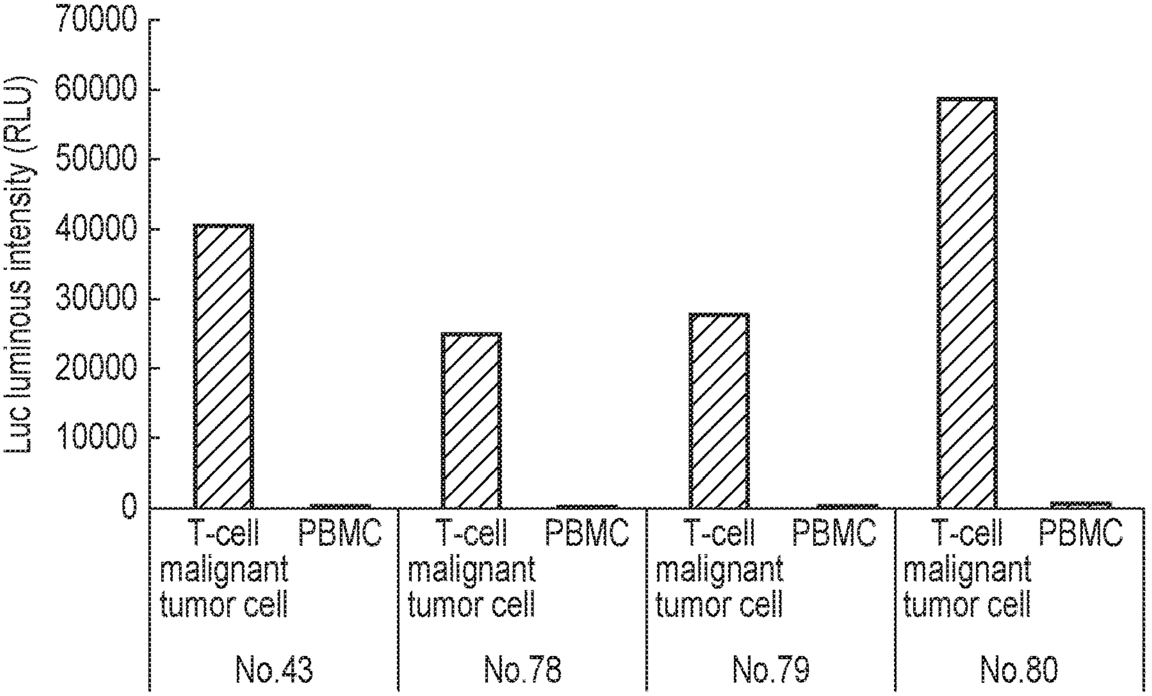
FIG. 12 is a graph showing experimental results of Example 2.

Measured results of the amount of luciferase luminescence are shown in FIG. 12. The luminescence intensity, in the case of No. 43 (FFT-20 (only)), was approximately 40000 RLU for the T-cell malignant tumor cell, and approximately 300 RLU for PBMC. The luminescence intensity, in the case of No. 78, was approximately 25000 RLU for T-cell malignant tumor cell, and approximately 100 RLU for PBMC. The luminescence intensity, in the case of No. 79, was approximately 27000 RLU for T-cell malignant tumor cell, and approximately 65 RLU for PBMC. The luminescence intensity, in the case of No. 80, was approximately 58000 RLU for T-cell malignant tumor cell, and approximately 640 RLU for PBMC.

All lipid particles were found that larger amounts thereof were incorporated into the T-cell malignant tumor cell, than in PBMC.

Example 3

In Vitro Evaluation of Lipid Particle Encapsulating iCaspase 9 mRNA

Preparation of Lipid Particle

RNA (Table 4, SEQ ID NO: 6) that contains a gene coding NanoLuc (registered trademark) luciferase (referred to as "NanoLuc™ gene", hereinafter) (Table 3, SEQ ID NO: 5); and RNA (Table 6, SEQ ID NO: 8) that contains a coding sequence of iCaspase 9 gene (Table 5, SEQ ID NO: 7) were synthetized by in vitro transcription method, and then a Cap structure and a poly(A) sequence were added respectively to the 5' terminal and the 3' terminal, to thereby synthesize mRNAs (RNA synthesis system, T7 mScript™ Standard mRNA production system, Cellscript™). In these mRNAs, a globin leader sequence is bound to the 5' terminal of the gene coding sequence, and a poly(A) sequence is bound to the 3' terminal.

TABLE 3

| NanoLu ™ Gene (SEQ ID NO: 5) | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 300 |
| gtgttcgacg gcaaaaagat cactgtaaca gggaccctgt ggaacggcaa caaaattatc | 420 |
| gacgagcgcc tgatcaaccc cgacggctcc ctgctgttcc gagtaaccat caacggagtg | 480 |
| accggctggc ggctgtgcga acgcattctg gcgtaa | 516 |

TABLE 4

RNA (Globin Leader + NanoLuc ™ Gene mRNA + Poly-A: SEQ ID NO: 6)

| | |
|---|---|
| gggagacaag cuugaauaca agcuacuugu ucuuuuugca cccgaacgga aguguuacuu | 60 |
| cugcucuaaa agcugcggaa uuguaccccu agcguuuaaa cuuaagcuug gcaauccggu | 120 |
| acuguuggua aagccaccau ggucuucaca cucgaagauu ucguugggga cuggcgacag | 180 |
| acagccggcu acaaccugga ccaaguccuu gaacagggag guguguccag uuuguuucag | 240 |
| aaucucgggg uguccguaac uccgauccaa aggauugucc ugagcgguga aaaugggcug | 300 |
| aagaucgaca uccaugucau caucccguau gaaggacuga gcggcgacca aaugggccag | 360 |
| aucgaaaaaa uuuuuaaggu gguguacccu guggaugauc aucacuuuaa ggugauccug | 420 |
| cacuauggca cacugguaau cgacggggUU acgccgaaca ugaucgacua uuucggacgg | 480 |
| ccguaugaag gcaucgccgu guucgacggc aaaaagauca cuguaacagg gacccugugg | 540 |
| aacggcaaca aaauuaucga cgagcgccag aucaaccccg acggcucccu gcuguuccga | 600 |
| guaaccauca acggagugac cggcuggcgg cugugcgaac gcauucuggc guaaggccgc | 660 |
| gacucuagaa caacaacaau ugcauucauu uuauguuuca gguucagggg gaggugUggg | 720 |
| agguuuuuuc ggaucaucua gaggaucccc gggcgagcuc ccaaaaaaaa aaaaaaaaaa | 780 |
| aaaaaaaaaa aaccg | 795 |

TABLE 5 iCaspase 9 Gene (SEQ ID NO: 7)

| | |
|---|---|
| atgctcgagg gagtgcaggt ggaaaccatc tccccaggag acgggcgcac cttccccaag | 60 |
| cgcggccaga cctgcgtggt gcactacacc gggatgcttg aagatggaaa gaaagttgat | 120 |
| tcctcccggg acagaaacaa gccctttaag tttatgctag gcaagcagga ggtgatccga | 180 |
| ggctgggaag aaggggttgc ccagatgagt gtgggtcaga gagccaaact gactatatct | 240 |
| ccagattatg cctatggtgc cactgggcac ccaggcatca tcccaccaca tgccactctc | 300 |
| gtcttcgatg tggagcttct aaaactggaa tctggcggtg gatccggagt cgacggattt | 360 |
| ggtgatgtcg gtgctcttga gagtttgagg ggaaatgcag atttggctta catcctgagc | 420 |
| atggagccct gtggccactg cctcattatc aacaatgtga acttctgccg tgagtccggg | 480 |
| ctccgcaccc gcactggctc caacatcgac tgtgagaagt tgcggcgtcg cttctcctcg | 540 |
| ctgcatttca tggtggaggt gaagggcgac ctgactgcca agaaaatggt gctggctttg | 600 |
| ctggagctgg cgcagcagga ccacggtgct ctggactgct gcgtggtggt cattctctct | 660 |
| cacggctgtc aggccagcca cctgcagttc ccaggggctg tctacggcac agatggatgc | 720 |
| cctgtgtcgg tcgagaagat tgtgaacatc ttcaatggga ccagctgccc cagcctggga | 780 |
| gggaagccca agctcttttt catccaggcc tgtggtgggg agcagaaaga ccatgggttt | 840 |
| gaggtggcct ccacttcccc tgaagacgag tcccctggca gtaaccccga gccagatgcc | 900 |
| accccgttcc aggaaggttt gaggaccttc gaccagctgg acgccatatc tagtttgccc | 960 |
| acacccagtg acatctttgt gtcctactct actttcccag gttttgtttc ctggagggac | 1020 |
| cccaagagtg gctcctggta cgttgagacc ctggacgaca tctttgagca gtgggctcac | 1080 |
| tctgaagacc tgcagtccct cctgcttagg gtcgctaatg ctgtttcggt gaaagggatt | 1140 |
| tataaacaga tgcctggttg ctttaatttc ctccggaaaa aacttttctt taaaacatca | 1200 |
| gctagctag | 1209 |

TABLE 6

| RNA (Globin Leader + iCaspase 9 Gene mRNA + Poly-A: SEQ ID NO: 8) | | | | | |
|---|---|---|---|---|---|
| gggagacaag | cuugaauaca | agcuacuugu | ucuuuuugca | ccuguacgga | aguguuacuu | 60 |
| cugcucuaaa | agcugcggaa | uuguacccac | uuaauacgac | ucacuauagg | cuagacugcc | 120 |
| augcucgagg | gagugcaggu | ggaaaccauc | uccccaggag | acgggcgcac | cuuccccaag | 180 |
| cgcggccaga | ccugcguggu | gcacuacacc | gggaugcuug | aagauggaaa | gaaaguugau | 240 |
| uccucccggg | acagaaacaa | gcccuuuaag | uuuaugcuag | gcaagcagga | ggugauccga | 300 |
| ggcugggaag | aagggguugc | ccagaugagu | gugggucaga | gagccaaacu | gacuauaucu | 360 |
| ccagauuaug | ccuauggugc | cacugggcac | ccaggcauca | ucccaccaca | ugccacucuc | 420 |
| gucuucgaug | uggagcuucu | aaaacuggaa | ucuggcggug | gauccggagu | cgacggauuu | 480 |
| ggugaugucg | gugcucuuga | gaguuugagg | ggaaaugcag | auuuggcuua | cauccugagc | 540 |
| auggagcccu | guggccacug | ccucauuauc | aacaauguga | acuucugccg | ugaguccggg | 600 |
| cuccgcaccc | gcacuggcuc | caacaucgac | ugugagaagu | ugcggcgucg | cuucuccucg | 660 |
| cugcauuuca | ugguggaggu | gaagggcgac | cugacugcca | agaaaauggu | gcuggcuuug | 720 |
| cuggagcugg | cgcagcagga | ccacggugcu | cuggacugcu | gcgugguggu | cauucucucu | 780 |
| cacggcuguc | aggccagcca | ccugcaguuc | ccaggggcug | ucuacggcac | agauggaugc | 840 |
| ccugugucgg | ucgagaagau | ugugaacauc | uucaauggga | ccagcugccc | cagccuggga | 900 |
| gggaagccca | agcucuuuuu | cauccaggcc | uguggguggg | agcagaaaga | ccauggguuu | 960 |
| gagguggccu | ccacuucccc | ugaagacgag | uccccuggca | guaaccccga | gccagaugcc | 1020 |
| accccguucc | aggaagguuu | gaggaccuuc | gaccagcugg | acgccauauc | uaguuugccc | 1080 |
| acacccagug | acaucuuugu | guccaucucu | acuuucccag | guuuuguuuc | cuggagggac | 1140 |
| cccaagagug | gcuccuggua | cguugagacc | cuggacgaca | ucuuugagca | gugggcucac | 1200 |
| ucugaagacc | ugcagucccu | ccugcuuagg | gucgcuaaug | cuguuucggu | gaaagggauu | 1260 |
| uauaaacaga | ugccugguug | cuuuaauuuc | cuccggaaaa | aacuuuucuu | uaaaacauca | 1320 |
| gcuagcuaga | ggauccccgg | gcgagcuccc | aaaaaaaaaa | aaaaaaaaaa | aaaaaaaaaa | 1380 |
| ccg | | | | | | 1383 |

Using lipid particles No. 43 and No. 79 previously used in Example 2, lipid particles encapsulating the mRNA of iCaspase 9 were prepared in the same way as in Example 2.

The T-cell malignant tumor cells used here were human leukemia cell line: Jurkat (from JRCB Cell Bank) and CCRF-CEM (from JRCB Cell Bank). A firefly luciferase-labeled Jurkat cell was prepared by introducing a firefly luciferase gene into the aforementioned Jurkat cell. A normal blood cell used here was a human peripheral blood mononuclear cell: PBMC (from a healthy donor).

On a 48-well culture plate, Jurkat, CCRF-CEM and PBMC were seeded at $5 \times 10^5$ cells/500 μL of TexMACS™ medium (from Miltenyi Biotec) each, to which 2 μg of the lipid particle encapsulating iCaspase 9 mRNA was added, the content was thoroughly mixed by pipetting, and then cultured in an incubator with a conditioned atmosphere of 37° C. and 5% $CO_2$. Twenty-four hours after, the culture plate was taken out, and CID (Chemical Inducer of Dimerization) (B/B Homodimerizer, from Takara Bio Inc.) was added to the wells for inducing cell death to adjust the final concentration to 10 nM.

After addition of CID, culture was continued in an incubator with a conditioned atmosphere of 37° C. and 5% $CO_2$, the cell was collected 24 hours after, and induction of cell death by the lipid particle encapsulating iCaspase 9 mRNA and CID was examined. The cell death was measured by flow cytometry.

Results

Figure 13:
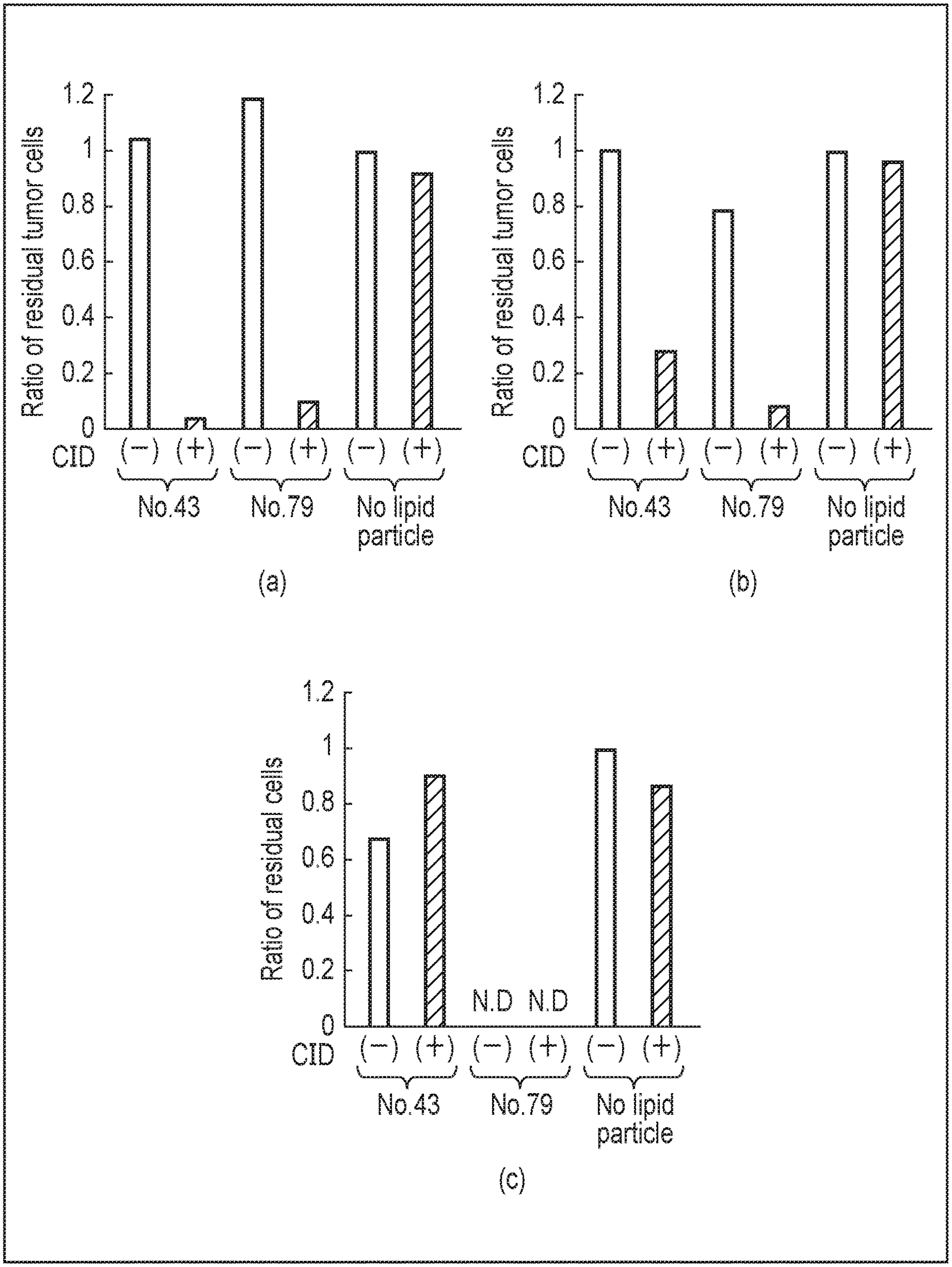
FIG. 13 is a graph showing experimental results of Example 3.

Results are summarized in FIG. 13 part (a) to part (c). In the graphs of FIG. 13, the ordinate plots ratio of the number of cultured tumor cells, with the number of tumor cells at the start day being 1. As shown in FIG. 13 part (a), the number of T-cell malignant tumor cell Jurkat distinctively decreased in the group having lipid particle No. 43 and CID administered, and in the group having lipid particle No. 79 and CID administered, which numbered 0.05 times and 0.1 times, respectively. As shown in FIG. 13 part (b), also the number of T-cell leukemia cell CCRF-CEM distinctively decreased in the group having lipid particle No. 43 and CID administered, and in the group having lipid particle No. 79 and CID administered, which numbered 0.3 times and 0.1 times, respectively. As shown in FIG. 13 part (c), the number of PBMC showed almost no decrease in the group having lipid particle No. 43 and CID administered (no data for the groups with administration of lipid particle No. 79, together with and without CID). In addition, all types of cell showed almost no decrease of the number of tumor cells, when mRNA was not encapsulated in the lipid particles.

It was thus demonstrated that the tumor cells can be reduced by using lipid particles No. 43 and No. 79 encapsulating iCaspase 9 mRNA, together with CID.

Example 4

In Vivo Evaluation of Lipid Particle Encapsulating iCaspase 9 mRNA

Preparation of Lipid Particle

Lipid particle No. 43 encapsulating the mRNA of NanoLuc™ described in Example 3 (nLuc-43), lipid particle No. 43 encapsulating the mRNA of iCaspase 9 described in Example 3 (iCas-43), and No. 79 lipid particle encapsulating the mRNA of iCaspase 9 (iCas-79) were prepared in the same way as in Example 2.

Administration to Mice and Measurement of Amount of Tumor

To immunodeficient mice (NOD. Cg-Prkdc$^{scid}$Il2rg$^{tmlWjl}$/SzJ NSG mouse), $3\times10^6$ cells/animal of ffLuc-labeled Jurkat cell were administered through the tail vein, and 4 days after, 15 days after, and 29 days after the administration, lipid particle No. 43 encapsulating the mRNA of NanoLuc™ (nLuc-43), lipid particle No. 43 encapsulating the mRNA of iCaspase 9 (iCas-43), and lipid particle No. 79 encapsulating the mRNA of iCaspase 9 (iCas-79) described in Example 3 were administrated, through the tail vein. One, two and three days after the administration of the mRNA-encapsulated lipid particles, 50 μg/animal of CID was intraperitoneally administered. The amount of tumor was evaluated in vivo in a time-dependent and quantitative manner, by administering a luciferin substrate intraperitoneally to the mice, and 10 minutes after, by measuring luminescence intensity using IVIS (registered trademark) Imaging System.

Results

Figure 14:
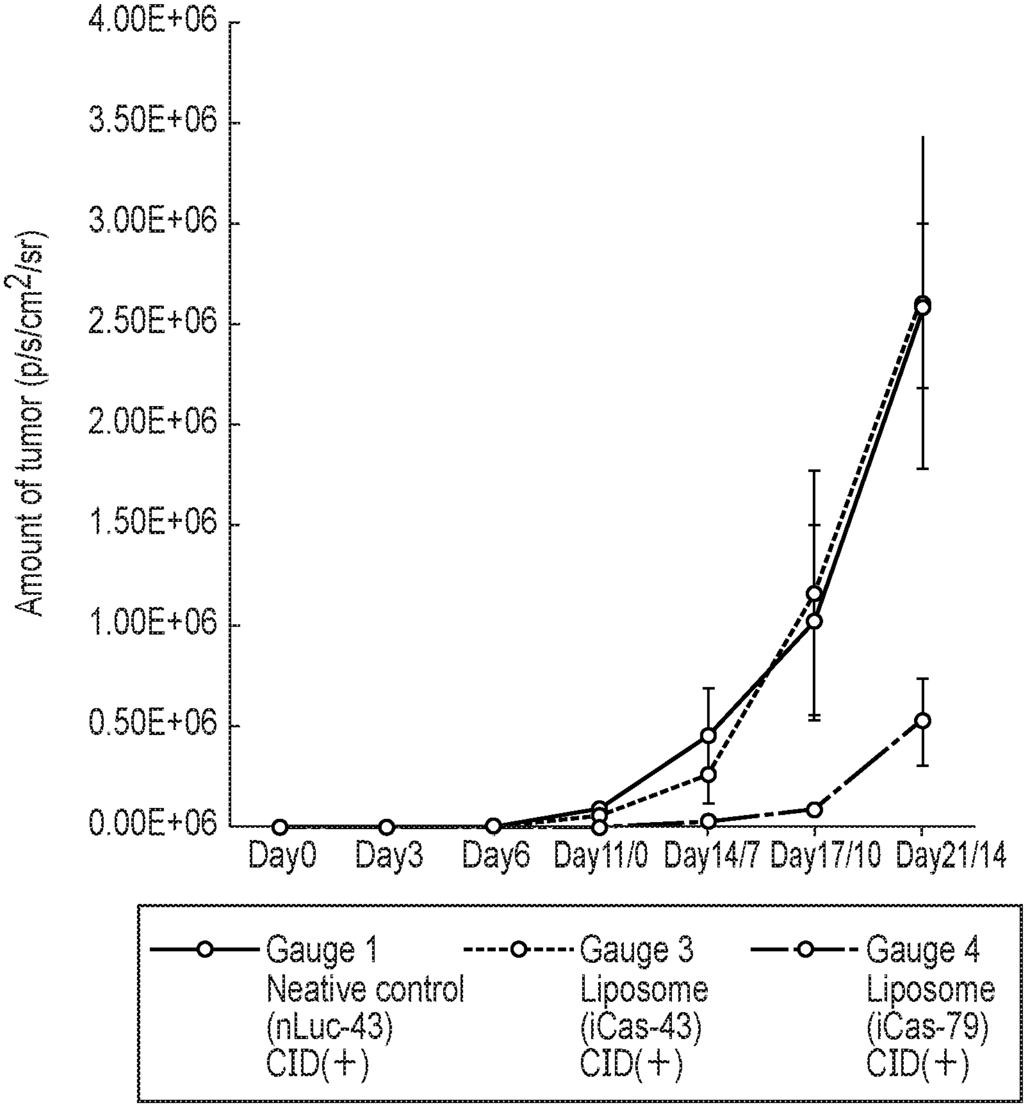
FIG. 14 is a graph showing experimental results of Example 4.

Results are shown in FIG. 14. FIG. 14 shows average values of the amount of tumor at the individual days of measurement. The mice administered nLuc-43 and iCas-No. 43 were found to have an amount of tumor of approximately 2600000 (p/s/cm$^2$/sr) on the 21st day (where, "p" stands for photon, and "s" stands for second, "sr" stands for steradian). On the other hand, the mice administered iCas-79 were found to have an amount of tumor of approximately 500000 (p/s/cm$^2$/sr) on the 21st day, being suppressed to one-fifth or around of the case with No. 43.

Given in vivo, unlike in vitro, the lipid particle can contact with the T-cell malignant tumor cell through various tissues such as vein inside the body, and the cells exist other than the T-cell malignant tumor cell, differences in the particle size and permeability between No. 79 and No. 43 made the test results different shown in FIG. 14.

Example 5

Evaluation of Particle Size

The particle size of the lipid particle encapsulating mRNA was measured using a zeta sizer (Zetasizer Nano ZSP, from Malvern Panalytical Ltd.). To 890 L of purified water (from Otsuka Pharmaceutical Co., Ltd.), 10 μL of the lipid particle encapsulating mRNA was mixed, and the particle size of the lipid particle was measured using Zetasizer in the particle size measurement mode. Table 7 shows results of particle size measurement of No. 43 and No. 79.

TABLE 7

Particle Size of Lipid Particle

| Composition of lipid particle | Particle size (nm) |
|---|---|
| No. 43 | 99.6 ± 6.1 |
| No. 79 | 89.7 ± 9.5 |

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A composition suitable for delivering an objective substance to a T-cell malignant tumor cell, the composition comprising:

a substance delivery carrier comprising a lipid particle and the objective substance encapsulated in the lipid particle, wherein the lipid particle comprises, as constituents thereof, at least a first lipid represented by formula (I), and a second lipid represented by formula (II):

(I)

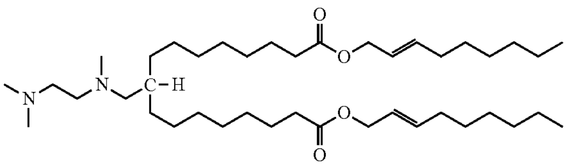

-continued (II)

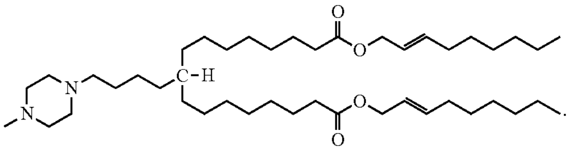

2. The composition of claim 1, wherein, in the constituents of the lipid particle, a compounding ratio of the second lipid accounts for a 40% mole ratio or more of a first fraction, wherein the first fraction consists of the first lipid and the second lipid.

gene, Bax gene, Bak gene, Bim gene, Bid gene, Bad gene, Noxa gene, Puma gene, Smac gene, DIABLO gene and HSV-TK gene.

8. The composition of claim 1 in a form suitable for detecting the T-cell malignant tumor cell.

9. The composition of claim 1 in a form suitable for diagnosing T-cell malignancy in a subject.

10. The composition of claim 8, wherein the objective substance is a diagnostic agent that generates a first signal.

11. The composition of claim 1, wherein the lipid particle further encapsulates a pH adjustor, osmoregulator, and/or gene activator.

12. A lipid particle manufacturing kit for delivering an objective substance to T-cell malignant tumor cell, the kit comprising:

a lipid mixture that comprises at least a first lipid represented by formula (I) and a second lipid represented by formula (II):

(I)

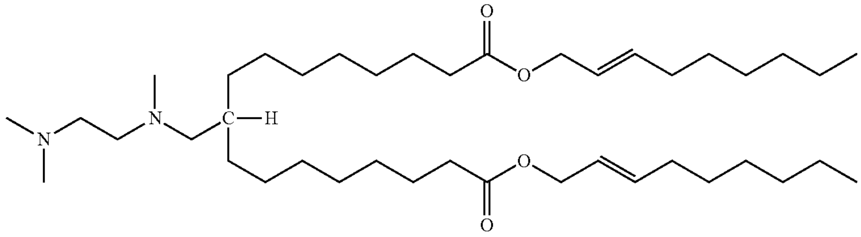

(II)

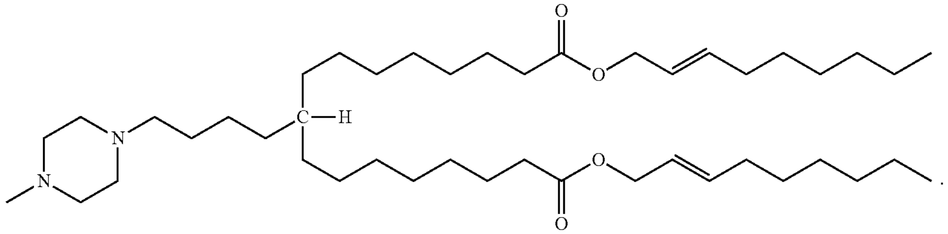

3. The composition of claim 1, wherein the lipid particle further comprises, as the constituents, at least one of a cationic lipid, neutral lipid, anti-aggregation lipid and cholesterol.

4. The composition of claim 1, in a form suitable for reducing or extinguishing the T-cell malignant tumor cell.

5. The composition of claim 1 in a form suitable for treating the T-cell malignant tumor cell in a subject.

6. The composition of claim 1, wherein the objective substance comprises an mRNA of a cytocidal gene.

7. The composition of claim 6, wherein the cytocidal gene is at least one selected from the group consisting of iCaspase 9 gene, Caspase 9 gene, Caspase 3 gene, Caspase 6 gene, Caspase 7 gene, Caspase 8 gene, Caspase 10 gene, p53 gene, ARF gene, Rb gene, Fas gene, TNF gene, DR4 gene, DR5

13. The kit of claim 12, wherein, in the lipid mixture, a compounding ratio of the second lipid accounts for a 40% mole ratio or more of a first fraction, wherein the first fraction consists of the first lipid and the second lipid.

14. The kit of claim 12, further comprising the objective substance.

15. A method for delivering an objective substance to a T-cell malignant tumor cell, the method comprising:

contacting the composition of claim 1 with a T-cell malignant tumor cell, wherein the substance delivery carrier comprises a lipid particle, and the objective substance encapsulated in the lipid particle, and the lipid particle containing, as constituents thereof, at least a first lipid represented by formula (I), and a second lipid represented by formula (II)

(I)

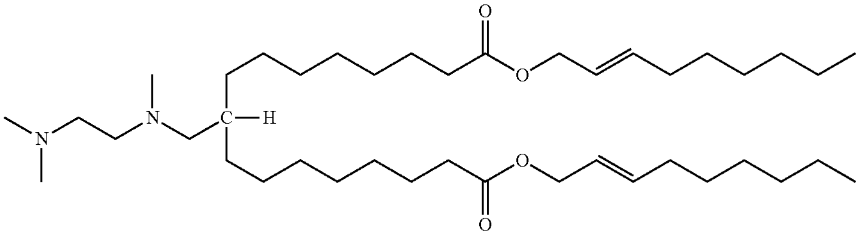

(II)

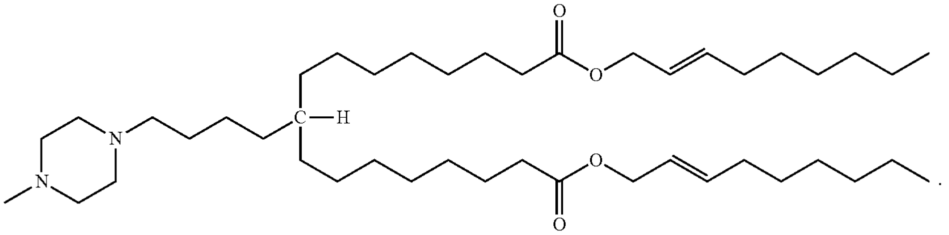

16. The method of claim 15, wherein the objective substance comprises an mRNA of a cytocidal gene.

17. The method of claim 15, wherein, in the constituents of the lipid particle, a compounding ratio of the second lipid accounts for 40% (mole ratio) or more of a first fraction, and the first fraction is composed of the first lipid and the second lipid.

18. The method of claim 15, wherein said contacting reduces or extinguishes the T-cell malignant tumor cell.

19. The method of claim 15, wherein the T-cell malignant tumor cell exists in vivo in a subject, the contacting is carried out by administering the composition to the subject, and a T-cell malignancy of the subject is treated by the contacting.

20. A method of detecting a T-cell malignant tumor cell, the method comprising:

contacting the composition of claim 1 that comprises the lipid particle and a diagnostic agent capable of generating a first signal and being encapsulated in the lipid particle, with a sample cell;

detecting a first signal; and determining presence or absence of T-cell malignant tumor cell in the sample cell on the basis of result of the detection, the lipid particle comprising, as constituents thereof, at least a first lipid represented by formula (I), and a second lipid represented by formula (II)

(I)

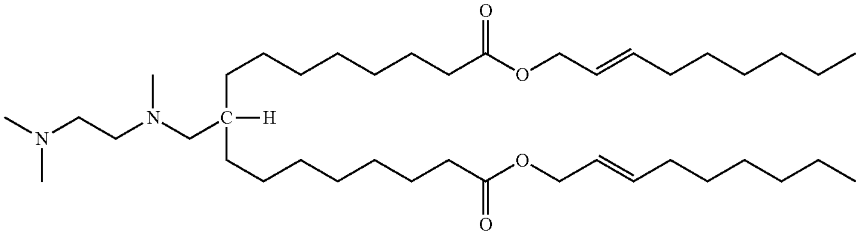

(II)

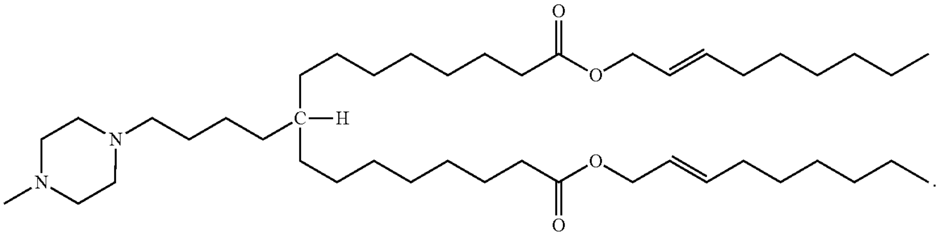

21. The method of claim 20, wherein, in the constituents of the lipid particle, a compounding ratio of the second lipid accounts for 40% (mole ratio) or more of a first fraction, wherein the first fraction consists of the first lipid and the second lipid.

22. The method of claim 20, wherein the sample cell is a cell that exists in vivo in the subject, and the method further comprises diagnosing whether the subject has a T-cell malignancy or not, on the basis of result of the detecting and/or result of the determining the presence of.

* * * * *